United States Patent
Tsuchiya et al.

(10) Patent No.: US 12,369,875 B2
(45) Date of Patent: Jul. 29, 2025

(54) MEDICAL IMAGE DIAGNOSTIC APPARATUS, MEDICAL IMAGE DIAGNOSTIC METHOD, AND STORAGE MEDIUM

(71) Applicant: Canon Medical Systems Corporation, Otawara (JP)

(72) Inventors: Nobuto Tsuchiya, Nasushiobara (JP); Michito Nakayama, Utsunomiya (JP)

(73) Assignee: Canon Medical Systems Corporation, Otawara (JP)

( * ) Notice: Subject to any disclaimer, the term of this patent is extended or adjusted under 35 U.S.C. 154(b) by 790 days.

(21) Appl. No.: 17/509,776

(22) Filed: Oct. 25, 2021

(65) Prior Publication Data

US 2022/0039771 A1 Feb. 10, 2022

Related U.S. Application Data

(62) Division of application No. 16/656,676, filed on Oct. 18, 2019, now Pat. No. 11,185,302.

(30) Foreign Application Priority Data

Oct. 24, 2018 (JP) .................................. 2018-200310
Oct. 15, 2019 (JP) .................................. 2019-188878

(51) Int. Cl.
*A61B 6/00* (2024.01)
*A61B 6/04* (2006.01)
(Continued)

(52) U.S. Cl.
CPC .......... *A61B 6/5276* (2013.01); *A61B 6/0407* (2013.01); *G06T 7/70* (2017.01); *A61B 6/032* (2013.01); *G06T 2207/20081* (2013.01)

(58) Field of Classification Search
USPC ........................................ 382/103, 128, 155
See application file for complete search history.

(56) References Cited

U.S. PATENT DOCUMENTS 7,639,782 B2 * 12/2009 Zelnik ...................... A61B 6/04
  600/407
7,857,513 B2 * 12/2010 Li ......................... A61B 6/0487
  378/207

(Continued)

FOREIGN PATENT DOCUMENTS

JP  2002159485 A  6/2002
JP  2002-224098 A  8/2002

(Continued)

OTHER PUBLICATIONS

Authors et al.: Disclosed Without Attribution, Automatic Table Height Optimizing Technique for Medical Imaging Systems, An IP.com Prior Database Technical Disclosure, IP.com No. IPCOM000213347D, pp. 1-6. (Year: 2011).*

(Continued)

*Primary Examiner* — Ishrat I Sherali
(74) *Attorney, Agent, or Firm* — Oblon, McClelland, Maier & Neustadt, L.L.P.

(57) ABSTRACT

A medical image diagnostic apparatus of embodiments includes an acquisition unit and a processing unit. The acquisition unit acquires physical characteristics data of an examination subject and information about an imaging target portion. The processing unit is configured to output bed position information about the examination subject according to the acquired physical characteristics data and the information about the imaging target portion by inputting the physical characteristics data and the information about the imaging target portion acquired by the acquisition unit to a trained model which is configured to output bed position (Continued)

information on the basis of physical characteristics data and information about a imaging target portion.

9 Claims, 18 Drawing Sheets

(51) Int. Cl.
*G06T 7/70* (2017.01)
*A61B 6/03* (2006.01)

(56) References Cited

U.S. PATENT DOCUMENTS

| | | | | |
|---|---|---|---|---|
| 9,226,719 | B2* | 1/2016 | Goto | A61B 6/589 |
| 10,783,655 | B2* | 9/2020 | Zhao | G06T 7/70 |
| 11,185,302 | B2* | 11/2021 | Tsuchiya | G06T 7/70 |
| 2006/0241387 | A1 | 10/2006 | Nagamine | |
| 2007/0053503 | A1* | 3/2007 | Zelnik | A61B 6/04 |
| | | | | 378/205 |
| 2008/0016620 | A1 | 1/2008 | Haras | |
| 2010/0094850 | A1* | 4/2010 | Oogami | G16H 40/63 |
| | | | | 378/197 |
| 2013/0142303 | A1* | 6/2013 | Goto | A61B 6/0487 |
| | | | | 378/19 |
| 2015/0362566 | A1 | 12/2015 | Haider | |
| 2017/0112416 | A1 | 4/2017 | Hao | |
| 2019/0318497 | A1 | 10/2019 | Zhao | |

FOREIGN PATENT DOCUMENTS

| | | |
|---|---|---|
| JP | 2009-291281 A | 12/2009 |
| JP | 2010-94205 A | 4/2010 |
| JP | 2012-21900 A | 2/2012 |
| JP | 2012-213583 A | 11/2012 |

OTHER PUBLICATIONS

Japanese Office Action issued Oct. 10, 2023 in Japanese Patent Application No. 2019-188878, citing reference 1 therein, 3 pages.

* cited by examiner

| EXAMINATION SUBJECT ID | IMAGING PORTION | NAME | AGE | SEX | HEIGHT | WEIGHT | BODY FAT PERCENTAGE | CHEST GIRTH | ABDOMINAL CIRCUMFERENCE | SYMPTOM TO BE CAUTIOUS | ... |
|---|---|---|---|---|---|---|---|---|---|---|---|
| 000001 | CHEST | ○○ ○○ | ** | M | 17*.* | 6* | ** | ** | ** | THERE IS ABDOMINAL INFLATION | ... |
| 000002 | HEAD | ■■ ■■ | ** | F | 15*.* | 5* | ** | ** | ** | | ... |
| ... | ... | ... | ... | ... | ... | ... | ... | ... | ... | ... | ... |

| AGE | SEX | HEIGHT | WEIGHT | ... |
|---|---|---|---|---|
| ... | ... | ... | ... | |
| 10-19 | M | ... | ... | |
| 20-29 | M | TALL (175cm OR MORE) | 70kg OR MORE | |
| 20-29 | M | TALL (175cm OR MORE) | 55-70kg | |
| 20-29 | M | TALL (175cm OR MORE) | 55kg OR LESS | |
| 20-29 | M | NORMAL (165-175cm) | ... | |
| 20-29 | M | SHORT (165cm OR LESS) | ... | |
| 30-39 | M | ... | ... | |
| ... | ... | ... | ... | |

NEW ←——————————→

| EXAMINATION SUBJECT | SEX | HEIGHT (cm) | AGE | WEIGHT (kg) | BODY FAT PERCENTAGE (%) | CONTRAST RADIOGRAPHY | HF/FF | BED POSITION | ... |
|---|---|---|---|---|---|---|---|---|---|
| A | M | 180 | 35 | 70 | 20 | ABSENCE | HF | (ya, za) | ... |
| B | M | 168 | 33 | 73 | 20 | ABSENCE | HF | (yb, zb) | ... |
| C | M | 178 | 52 | 74 | 20 | ABSENCE | HF | (yc, zc) | ... |
| D | M | 176 | 33 | 65 | 19 | ABSENCE | HF | (yd, zd) | ... |
| E | M | 180 | 34 | 72 | 11 | ABSENCE | HF | (ye, ze) | ... |
| F | M | 178 | 33 | 73 | 19 | PRESENCE | HF | (yf, zf) | ... |
| G | M | 178 | 33 | 73 | 18 | ABSENCE | FF | (yg, zg) | ... |
| ... | ... | ... | ... | ... | ... | ... | ... | ... | ... |
| X | M | 178 | 33 | 73 | 19 | ABSENCE | HF | | ... |

41-1

| EXAMINATION SUBJECT | SEX | HEIGHT (cm) | AGE | WEIGHT (kg) | BODY FAT PERCENTAGE (%) | CONTRAST RADIOGRAPHY | HF/FF |
|---|---|---|---|---|---|---|---|
| P | M | 178 | 33 | 73 | 19 | ABSENCE | HF |

US 12,369,875 B2

MEDICAL IMAGE DIAGNOSTIC APPARATUS, MEDICAL IMAGE DIAGNOSTIC METHOD, AND STORAGE MEDIUM

CROSS-REFERENCE TO RELATED APPLICATION

This application is a divisional of application Ser. No. 16/656,676, filed Oct. 18, 2019, which claims priority to Japanese Patent Application No. 2019-188878, filed Oct. 15, 2019, and Japanese Patent Application No. 2018-200310, filed Oct. 24, 2018, the content of which is incorporated herein by reference.

BACKGROUND

Field

Embodiments of the present invention relate to a medical image diagnostic apparatus, a medical image diagnosis method, and a storage medium.

Background

Conventionally, in a medical image diagnostic apparatus such as an X-ray CT apparatus, a method for changing the height of a bed on the basis of a calculation result when calculating a height that enables an examination subject to easily get on and off according to the height of a subject has been disclosed.

In addition, in conventional medical imaging diagnostic apparatuses, a field of view (FOV) is set through manual operation in many cases and some time may be required for the operations thereof before imaging.

BRIEF DESCRIPTION OF THE DRAWINGS

FIG. 4 is a diagram showing an example of physical characteristics data and information about an imaging target portion stored in examination subject information.
FIG. 22 is a diagram showing processing of a processing function.

DETAILED DESCRIPTION

A medical image diagnostic apparatus of embodiments includes an acquisition unit and a processing unit The acquisition unit acquires physical characteristics data of an examination subject and information about an imaging target portion. The processing unit is configured to output bed position information with respect to the examination subject according to information about the acquired physical characteristics data and imaging target portion by inputting the physical characteristics data and the information about the imaging target portion acquired by the acquisition unit to a trained model which is configured to output bed position information on the basis of physical characteristics data and information about an imaging target portion.

Hereinafter, a medical image diagnostic apparatus, a medical image diagnosis method, and a storage medium of embodiments will be described with reference to the drawings. The medical image diagnostic apparatus is, for example, an apparatus that allows diagnosis to be performed on an examination subject by performing processing on medical images, such as an X-ray computed tomography (CT) apparatus, a positron emission tomography (PET) apparatus, a single photon emission computed tomography (SPECT) inspection apparatus or the like. Although description will be given in which the medical image diagnostic apparatus is an X-ray CT apparatus in a first embodiment and a third embodiment and a nuclear medical diagnostic apparatus such as a SPECT inspection apparatus in a second embodiment, the present invention is not limited thereto.

First Embodiment

Figure 1:
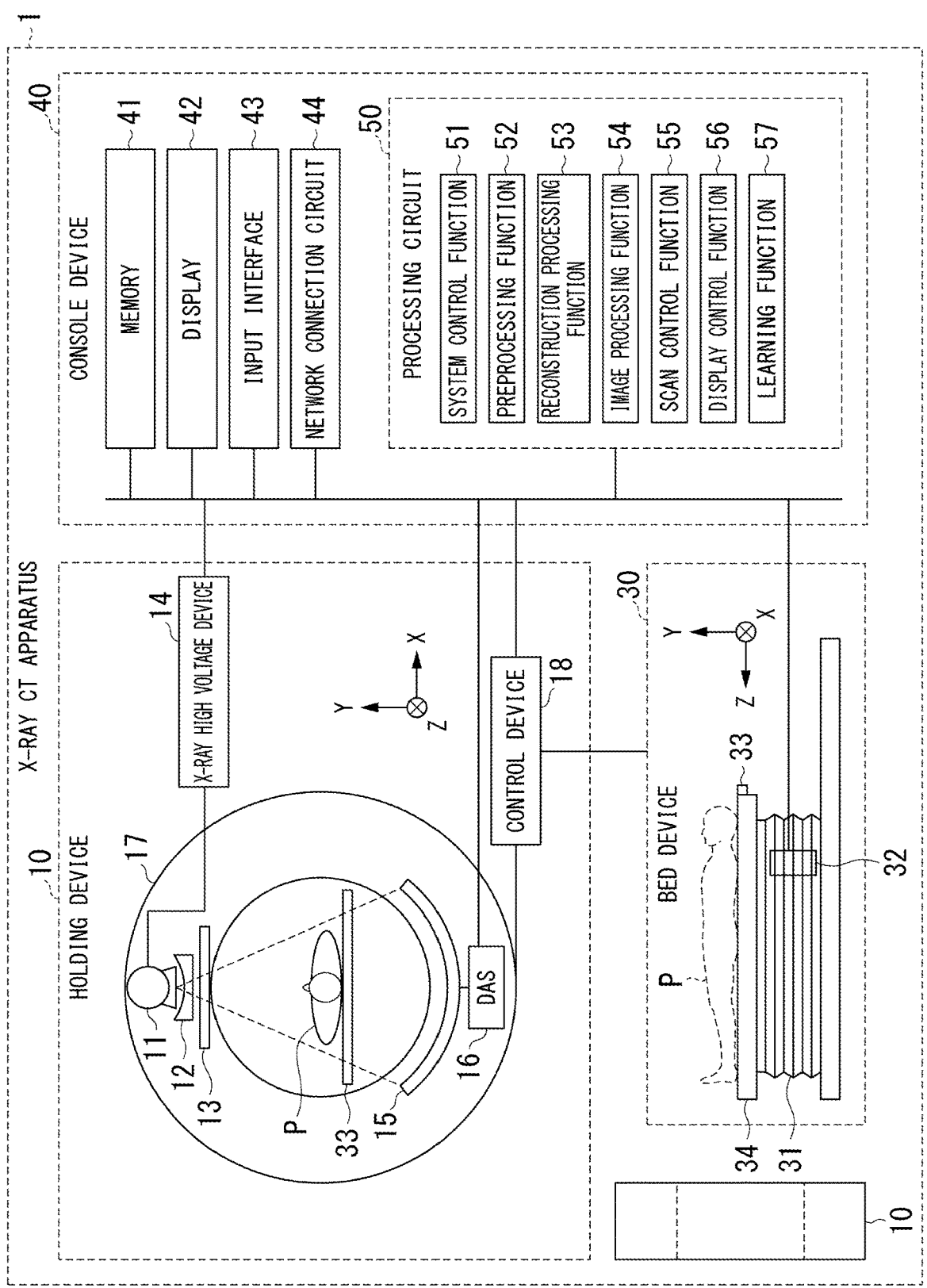
FIG. 1 is a configuration diagram of an X-ray CT apparatus according to a first embodiment.

FIG. 1 is a configuration diagram of an X-ray CT apparatus 1 according to a first embodiment. The X-ray CT apparatus 1 is an example of a medical image diagnostic apparatus. The X-ray CT apparatus 1 includes, for example, a holding device 10, a bed device 30, and a console device 40. Although FIG. 1 shows both a diagram of the holding device 10 viewed in a Z-axis direction and a diagram viewed in an X-axis direction for convenience of description, there is actually one holding device 10. In embodiments, a rotation axis of a rotary frame 17 in a non-tilted state or a longitudinal direction of a top board 33 of the bed device 30 is defined as a Z-axis direction, an axis at a right angle to the Z-axis direction that is parallel to the floor is defined as an X-axis direction, and a direction at a right angle to the Z-axis direction that is perpendicular to the floor is defined as a Y-axis direction.

The holding device 10 includes, for example, an X-ray tube 11, a wedge 12, a collimator 13, an X-ray high voltage device 14, an X-ray detector 15, a data collection system (hereinafter, data acquisition system (DAS) 16, the rotary frame 17 and a control device 18.

The X-ray lube 11 generates X rays by radiating thermions from a cathode (filament) to an anode (target) according to application of a high voltage from the X-ray high voltage device 14. The X-ray tube 11 includes a vacuum tube. For example, the X-ray tube 11 may be a rotating anode type X-ray tube which generates X rays by radiating thermions to a rotating anode.

The wedge 12 is a filter for controlling the amount of X rays radiated from the X-ray tube 11 to an examination subject P. The wedge 12 attenuates X rays transmitted through the wedge 12 such that a distribution of the amount of X rays radiated from the X-ray tube 11 to the examination subject P becomes a predetermined distribution. The wedge 12 is also called a wedge filter or a bow-tie filter. For example, the wedge 12 may be manufactured by processing aluminum such that it has a predetermined target angle and a predetermined thickness.

The collimator 13 is a mechanism for narrowing a radiation range of X rays that have been transmitted through the wedge 12. The collimator 13 narrows a radiation range of X rays, for example, by forming a slit according to combination of a plurality of lead plates. The collimator 13 may also be called an X-ray aperture.

The X-ray high voltage dev ice 14 includes, for example, a high voltage generation device and an X-ray control device. The high voltage generation device has an electrical circuit including a transformer (trans), a rectifier and the like and generates a high voltage to be applied to the X-ray tube 11. The X-ray control device controls an output voltage of the high voltage generation device in response to the amount of X rays generated by the X-ray tube 11. The high voltage generation device may perform voltage boosting through the aforementioned transformer or perform voltage boosting through an inverter. The X-ray high voltage device 14 may be provided in the rotary frame 17 or provided on the side of a fixed frame (not shown) of the holding device 10.

The X-ray detector 15 detects the intensity of X rays that have been generated by the X-ray tube 11, passed through the examination subject P and applied to the X-ray detector 15. The X-ray detector 15 output an electrical signal (an optical signal or the like is possible) in response to the detected intensity of X rays to the DAS 18. The X-ray detector 15 includes, for example, a plurality of X-ray detection element strings. The plurality of X-ray detection element strings are obtained by arranging a plurality of X-ray detection elements in a channel direction along an arc having the focus of the X-ray tube 11 as a center. The plurality of X-ray detection element strings are arranged in a slice direction (row direction).

The X-ray detector 15 is, for example, an indirect detector including a grid, a scintillator array and an optical sensor array. The scintillator array includes a plurality of scintillators. Each scintillator has scintillator crystals. Scintillator crystals emit an amount of light in response to the intensity of input X rays. The grid is disposed on a surface of the scintillator array to which X rays are input and includes an X-ray shielding plate having a function of absorbing scattered X rays. Meanwhile, there is a case in which the grid is called a collimator (one-dimensional collimator or two-dimensional collimator). The optical sensor array includes, for example, optical sensors such as photomultipliers (PMTs). The optical sensor array outputs an electrical signal in response to the amount of light emitted from the scintillators. The X-ray detector 15 may be a direct conversion type detector including a semiconductor element which converts input X rays into an electrical signal.

The DAS 16 includes, for example, an amplifier, an integrator, and an A/D converter. The amplifier performs amplification processing on an electrical signal output from each X-ray detection element of the X-ray detector 15. The integrator integrates amplified electrical signals over a view period (which will be described later). The A/D convener converts an electrical signal representing an integration result into a digital signal. The DAS 16 outputs detected data based on the digital signal to the console device 40. The detected data is a digital value of an X-ray intensity identified through a channel number and a siring number of an X-ray detection element that is a generation source, and a view number indicating a collected view. A view number is a number that varies according to rotation of the rotary frame 17 and is, for example, a number that increases according to rotation of the rotary frame 17. Accordingly, a view number is information representing a rotation angle of the X-ray tube 11. A view period is a period from a rotation angle corresponding to a certain view number to a rotation angle corresponding to the next view number. The DAS 16 may detect view switching through a timing signal input from the control device 18, an internal timer or a signal acquired from a sensor which is not shown. When X rays are continuously emitted by the X-ray tube 11 during full scanning, the DAS 16 collects detected data groups corresponding to the entire circumference (360 degrees). When X rays are continuously emitted by the X-ray tube 11 during half scanning, the DAS 16 collects detected data corresponding to half a circumference (180 degrees).

The rotary frame 17 is an annular member which supports the X-ray tube 11, the wedge 12, the collimator 13 and the X-ray detector 15 such that the X-ray tube 11, the wedge 12 and the collimator 13 face the X-ray detector 15. The rotary frame 17 is rotatably supported by a fixed frame having the examination subject P introduced thereinto as a center. The rotary frame 17 additionally supports the DAS 16. Detected data output from the DAS 16 is transmitted from a transmitter having a light emitting diode (LED) provided in the rotary frame 17 to a receiver having a photodiode provided in a non-rotary part (e.g., a fixed frame) of the holding device 10 through optical communication and forwarded to the console device 40 through the receiver. Meanwhile, a method of transmitting detected data from the rotary frame 17 to a non-rotary part is not limited to the aforementioned method using optical communication and any non-contact type transmission method may be employed. The rotary frame 17 is not limited to an annular member and may be a member such as an arm as long as it can support and rotate the X-ray tube 11 and the like.

Although the X-ray CT apparatus 1 may be, for example, a Rotate/Rotate-Type X-ray CT apparatus (third-generation CT) in which both the X-ray tube 11 and the X-ray detector 15 are supported by the rotary frame 17 and rotate around the examination subject P, it is not limited thereto and may be a Stationary/Rotate-Type X-ray CT apparatus (fourth-generation CT) in which a plurality of X-ray detection elements arranged in an annular shape are fixed to a fixed frame and the X-ray tube 11 rotates around the examination subject P.

The control device 18 includes, for example, a processing circuit having a processor such as a central processing unit (CPU) and a driving mechanism including a motor, an actuator and the like. The control device 18 receives an input signal from an input interface 43 attached to the console device 40 or the holding device 10 and controls operations of the holding device 10 and the bed device 30.

For example, the control device 18 may rotate the rotary frame 17, tilt the holding device 10 or move the top board 33 of the bed device 30. When the control device 18 tilts the holding device 10, the control device 18 rotates the rotary frame 17 on an axis parallel to the Z-axis direction on the basis of an inclination angle (tilt angle) input to the input interface 43. The control device 18 ascertains a rotation angle of the rotary frame 17 through an output of a sensor which is not shown, and the like. In addition, the control device 18 provides the rotation angle of the rotary frame 17 to the processing circuit 50 at any lime. The control device 18 may be provided in the holding device 10 or provided in the console device 40.

The bed device 30 mounts and moves live examination subject P to be scanned and introduces him or her into the rotary frame 17 of the holding device 10. The bed device 30 includes, for example, a base 31, a bed driving device 32, the top board 33, and a supporting frame 34. The base 31 includes a housing which supports the supporting frame 34 such that the supporting frame 34 can move in a vertical direction (Y-axis direction). The bed driving device 32 includes a motor and an actuator. The bed driving device 32 moves the top board 33 on which the examination subject P is mounted in the longitudinal direction (Z-axis direction) of the top board 33 along the supporting frame 34. The top board 33 is a plate-shaped member on which the examination subject P is mounted.

The bed driving device 32 may move the supporting frame 34 in the longitudinal direction of the top board 33 as well as the top board 33. Further, contrary to the above, the holding device 10 may be movable in the Z-axis direction and the rotary frame 17 may be controlled such that it comes near the examination subject P in accordance with movement of the holding dev ice 10. In addition, both the holding device 10 and the top board 33 may be configured such that they are movable.

The console device 40 includes, for example, a memory 41, a display 42, the input interface 43, a network connection circuit 44, and a processing circuit 50. Although the console device 40 is described as a body separate front the holding device 10 in embodiments, some or all components of the console dev ice 40 may be included in the holding device 10.

The memory 41 is realized, for example, by a semiconductor element such as a random access memory (RAM) or a flash memory, a hard disk, an optical disc, or the like. The memory 41 stores, for example, detected data, projection data, reconstructed images. CT images, and the like. Such data may be stored in an external memory with which the X-ray CT apparatus 1 can communicate instead of the memory 41 (or in addition to the memory 41). For example, the external memory may be controlled through a cloud server which manages the external memory by receiving a read request.

The display 42 displays various types of information. For example, the display 42 displays medical images (CT images) generated by a processing circuit, a graphical user interface (GUI) image through which various operations from an operator are received, and the like. For example, the display 42 may be a liquid crystal display, a cathode ray tube (CRT), an organic electroluminescence (EL) display, or the like. The display 42 may be provided in the holding device 10. The display 42 may be a desktop type or a display device (e.g., a tablet terminal) which can wirelessly communicate with the main body of the console device 40.

The input interface 43 receives various input operations from an operator and outputs electrical signals representing details of received input operations to the processing circuit 50. For example, the input interface 43 may receive operations of inputting collection conditions when detected data or projection data (which will be described later) is collected, reconstruction conditions when a CT image is reconstructed, image processing conditions when a postprocessing image is generated from a CT image, and the like. For example, the input interlace 43 may be realized by a mouse, a keyboard, a touch panel, a trackball, a switch, a button, a joystick, a fool pedal, a camera, an infrared sensor, a microphone, or the like. The input interface 43 may be provided in the holding device 10. In addition, the input interface 43 may be realized by a display device (e.g., a tablet terminal) which can wirelessly communicate with the main body of the console device 40.

The network connection circuit 44 includes, for example, a network card having a pruned circuit board, a wireless communication module, or the like. The network connection circuit 44 implements an information communication protocol in accordance with a network form of a connection target Networks include, for example, a local area network (LAN), a wide area network (WAN), the Internet, a cellular network, a dedicated line, and the like.

The processing circuit 50 controls the overall operation of the X-ray CT apparatus 1. The processing circuit 50 executes, for example, a system control function 51, a preprocessing function 52, a reconstruction processing function 53, an image processing function 54, a scan control function 55, a display control function 56, a learning function 57, and the like. For example, the processing circuit 50 may realize these functions by a hardware processor executing a program stored in the memory 41.

For example, the hardware processor may refer to a circuitry such as a CPU, a graphics processing unit (GPU), an application specific integrated circuit (ASIC), a programmable logic device (e.g., a simple programmable logic device (SPLD) or a complex programmable logic device (CPLD)) or a field programmable gate array (FPGA). A program may be directly incorporated into a hardware processor circuit instead of being stored in the memory 41. In this case, a hardware processor realizes functions by reading and executing a program incorporated into the circuit. A hardware processor is not limited to a single circuit as a configuration, and a plurality of independent circuits may be combined to constitute a single hardware processor to realize respective functions. In addition, respective functions may be realized by integrating a plurality of components into a single hardware processor.

Components included in the console device 40 or the processing circuit 50 may be distributed and realized by a plurality of hardware circuits. The processing circuit 50 may be realized by a processing device which can communicate with the console device 40 instead of being included in the console device 40. For example, the processing device may be a workstation connected to a single X-ray CT apparatus or a device (e.g., a cloud server) which is connected to a plurality of X-ray CT apparatuses and integrally executes processes equivalent to those of the processing circuit 50 which will be described below.

The system control function 51 controls various functions of the processing circuit 50 on the basis of input operations received by the input interface 43.

The processing function 52 performs preprocessing such as logarithmic conversion processing, offset correction processing, inter-channel sensitivity correction processing and beam hardening correction on detected data output from the DAS 16, generates projection data, and stores the generated projection data in the memory 41.

The reconstruction processing function 53 performs reconstruction processing through a filter correction reverse projection method, a sequential approximation reconstruction method or the like on projection data generated by the preprocessing function 52, generates a CT image and stores the generated CT image in the memory 41.

The image processing function 54 converts a CT image into a three-dimensional image or section image data with an arbitrary section through a known method on the basis of an input operation received by the input interface 43. Conversion into a three-dimensional image may be performed by the preprocessing function 52.

The scan control function 55 instructs the X-ray high voltage device 14, the DAS 16, the control device 18 and the bed driving device 32 to control detected data collection processing in the holding device 10. The scan control function 55 controls operation of each component when imaging for collecting scan images and imaging of images used for diagnosis are performed.

The display control function 56 controls a display mode of the display 42.

The learning function 57 learns position information of the bed dev ice 30. The learning function 57 will be described later. The learning function 57 is an example of a "learning unit."

According to the above-described configuration, the X-ray CT apparatus 1 scans the examination subject P in a mode such as helical scan, conventional scan or step-and-shot. The helical scan is a mode of rotating the rotary frame 17 while moving the top board 33 to scan the examination subject P in a spiral form. The conventional scan is a mode of rotating the rotary frame 17 in a state in which the top board 33 is slopped to scan the examination subject P in a circular orbit. The step-and-shot is a mode of moving the position of the top board 33 at specific intervals to perform the conventional scan in a plurality of scan areas.

Figure 2:
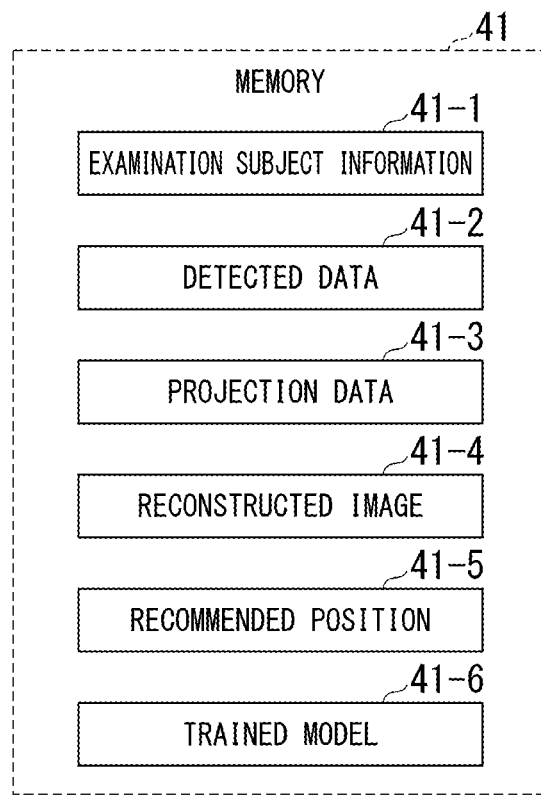
FIG. 2 is a diagram showing an example of data stored in a memory.

FIG. 2 is a diagram showing an example of data stored in the memory 41. As shown in FIG. 2, for example, information such as examination subject information 41-1, detected data 41-2, projection data 41-3, reconstructed images 41-4, recommended positions 41-5, trained models 41-6 and the like generated by the processing circuit 50 may be stored in the memory 41.

Figure 3:
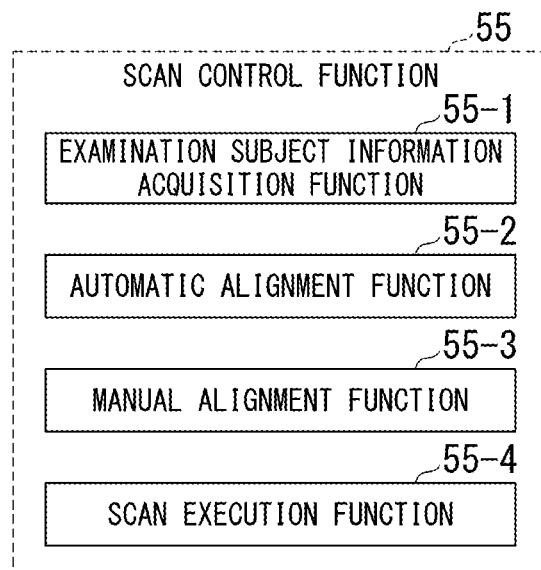
FIG. 3 is a configuration diagram of a scan control function.

FIG. 3 is a configuration diagram of the scan control function 55. The scan control function 55 includes, for example, an examination subject information acquisition function 55-1, an automatic alignment function 55-2, a manual alignment function 55-3 and a scan execution function 55-4.

The examination subject information acquisition function 55-1 acquires physical characteristics data and information about an imaging target portion associated with the examination subject P through the examination subject information 41-1 and outputs the acquired physical characteristics data and information about the imaging target portion to the automatic alignment function 55-2. The examination subject information acquisition function 55-1 is an example of the "acquisition unit." Further, the examination subject information acquisition function 55-1 may receive input of physical characteristics data and information about an imaging target portion input by an operator through the input interface 43 and acquire details of the input.

FIG. 4 is a diagram showing an example of physical characteristics data and information about an imaging target portion stored in the examination subject information 41-1. The examination subject information 41-1 includes, for example, physical characteristics data of an examination subject (e.g., information about an ID for identifying the examination subject, a sex end an age, and actual measurement values such as a height, a weight, a chest girth and an abdominal circumference) and information about a imaging target portion (e.g., a head, a chest or the like). Correct values (actual measurement values) of the examination subject P may be input or estimated values may be set by an operator as the physical characteristics data.

Figure 12:
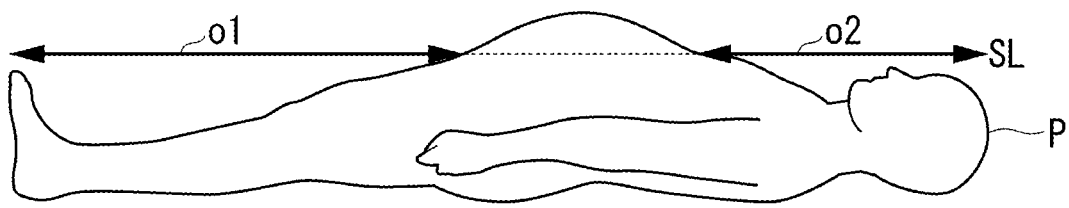
FIG. 12 is a diagram showing a problem occurring in an image diagnostic apparatus of a reference example.

Further, the examination subject information 41-1 may include test purposes and precaution information of the examination subject P. The examination subject information 41-1 includes, for example, test purposes such as "medical checkup" and "periodic health examination," the names of diseases in therapy or possible diseases, and precaution information such as "there is abdominal inflation," "there is no abdominal inflation" or the like. When the trained model 41-6 does not consider a state in which the abdomen of the examination subject P has inflated as shown in FIG. 12 which will be described later, an output recommended position is likely to be separated from a imaging position suitable for the examination subject P even when conditions such as the height and the weight are satisfied. Accordingly when the trained model 41-6 is selected through the automatic alignment function 55-2, it may be desirable to refer to the test purpose and symptoms of the examination subject P.

Referring back to FIG. 3, the automatic alignment function 55-2 assists alignment by setting a recommended position of the top board 33 on the basis of physical characteristics data and information about an imaging target portion output from the examination subject information acquisition function 55-1. Alignment will be described later. The automatic alignment function 55-2 sets a recommended position of the top board 33 by selecting a trained model 41-6 generated by the learning function 57 which will be described later depending on the physical characteristics data such as the height and weight of the examination subject P, and the like and inputting the physical characteristics data of the examination subject P and the information about the imaging target portion to the selected trained model 41-6. The automatic alignment function 55-2 selects, for example, a trained model 41-6 trained using the physical characteristics data of the examination subject P and data close to the imaging target portion. If it does not exist, the manual alignment function 55-3 receives an input of an operator of the X-ray CT apparatus 1 and performs alignment as will be described later.

The trained model 41-6 is prepared, for example, for each of a plurality of groups in which labels have been provided to the age, sex, height, weight, an imaging target portion and the like of the examination subject P, which will be described later. The automatic alignment function 55-2 selects a trained model 41-6 corresponding to a group matching the age, sex, height, weight, an imaging target portion and the like of the examination subject P.

A recommended position of the top board 33 includes, for example, the height with respect to a reference position of the top board 33 and a positional relation between the top board 33 and the holding device 10 (or a positional relation between the examination subject P and the holding device 10) immediately before imaging of the examination subject P is started. A recommended position of the top board 33 may include a height with respect to the reference position of the top board 33 and a positional relation between the top board 33 and the folding device 10 at each of timings such as a timing at which the examination subject P gets on or off the top board 33 or a liming before imaging is started (e.g., timing of imaging preparation such as fixture setting). The reference position may be a floor on which the bed device 30 is installed or a lowest position at which the top board 33 can be placed. The automatic alignment function 55-2 stores a recommended position of the top board 33 in the memory 41 as a recommended position 41-5. The automatic alignment function 55-2 is an example of the "processing unit."

It is desirable that the automatic alignment function 55-2 provide some trigger operations (e.g., a lock release operation performed by an operator and an audio guidance for indicating movement of the top board 33) in order to call attention of the operator and the examination subject P on the top board 33 before movement of the top board 33 to the recommended position is started.

Meanwhile, when there is no trained model 41-6 suitable for the examination subject P, the automatic alignment function 55-2 may give up setting of a recommended position of the top board 33 and allow the manual alignment function 55-3 to proceed with processing.

Figure 5:
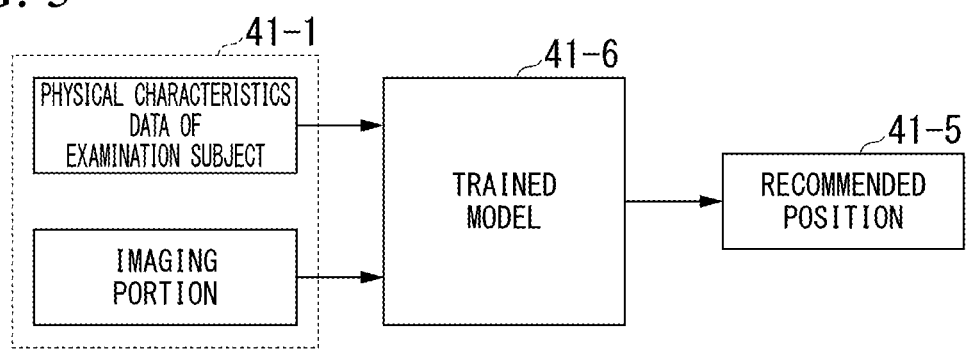
FIG. 5 is a diagram showing output processing performed by a trained model.

FIG. 5 is a diagram showing output processing performed by the trained model 41-6. The automatic alignment function 55-2 outputs a recommended position stored in the recommended position 41-5 of the top board 33 by inputting the physical characteristics data of the examination subject P and information about the imaging target portion to the trained model 41-6 as parameters. It is possible to reduce an alignment time required until the examination subject P is imaged (scanned) by performing subsequent processing on the basis of the recommended position. The automatic alignment function 55-2 stores the recommended position 41-5 roughly set in this manner in the memory 41.

The manual alignment function 55-3 receives an input of an operator of the X-ray CT apparatus 1 with respect to whether the recommended position set by the automatic alignment function 55-2 will be used. The input received here includes an input for the purpose of realignment and an input for the purpose of fine adjustment. The manual alignment function 55-3 receives an input operation of the operator for realignment or fine adjustment and controls the operation of the top board 33. The manual alignment function 55-3 reflects a result of realignment or fine adjustment in the recommended position 41-5.

Hereinafter, alignment performed by the automatic alignment function 55-2 and the manual alignment function 55-3 will be described. Alignment is to move the top board 33 to an imaging start position after the examination subject P has taken an imaging posture on the top board 33.

When manual alignment is performed, the operator of the X-ray CT apparatus 1 moves the top board 33 by operating the input interface 43 such as a button or a foot pedal and moves the examination subject P to a imaging start position (in a state in which a portion to be imaged is included between the X-ray tube 11 and the DAS 16). The X-ray CT apparatus 1 assists alignment performed by the operator, for example, by radiating an irradiation lamp (laser light) for alignment. For example, the operator of the X-ray CT apparatus 1 may align an FOV center while checking a state in which an irradiation lamp for alignment in the Z-axis direction of the holding device 10 has been aligned with the lateral center line of the body of the examination subject P and then checking a state in which an mediation lamp for alignment in the X-axis direction has been aligned with a portion (e.g., the eyes, ears, sternoclavicular joint or the like of the examination subject P) used for alignment. The automatic alignment function 55-2 which will be described later can alleviate a labor required for this alignment and efficiently perform operations before imaging.

Referring back to FIG. 3, the scan execution function 55-4 performs imaging at a position of the top board 33 set by the manual alignment function 55-3 to acquire a CT image. The scan execution function 55-4 stores the acquired captured image in the form of detected data 41-2, projection data 41-3, a reconstructed image 41-4 or the like.

Hereinafter, processing performed by the learning function 57 will be described. The learning function 57 acquires sets of physical characteristics data of a plurality of examination subjects and information about imaging target portions from the memory 41 or an external device. The learning function 57 generates a trained model 41-6 by performing machine learning using the acquired physical characteristics data of examination subjects and information about imaging target portions as learning data and using position information of the top board 33 set for the same examination subject as teacher data. The learning function 57 is in example of a "model generation unit." In addition, the learning function 57 may be realized by an external device.

Figure 6:
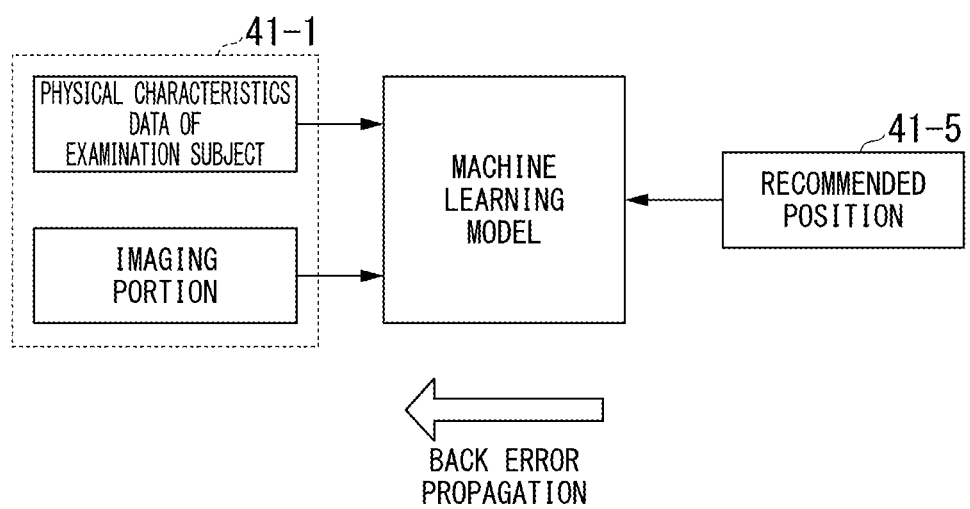
FIG. 6 is a diagram showing processing of a learning function.

FIG. 6 is a diagram showing processing of the learning function 57. The learning function 57 inputs learning data of a plurality of sets to a machine learning model in which connection information and the like have been defined in advance and parameters such as a connection coefficient have been provisionally set and adjusts parameters in the machine learning model such that the result of input becomes close to teacher data corresponding to the learning data. For example, the learning function 57 may generate a machine learning model for generating a trained model using physical characteristics data of a certain examination subject and information about a imaging target portion included in the examination subject information 41-1 as learning data and using position information of the top board 33 when the examination subject is imaged included in the recommended position 41-5 as teacher data.

The learning function 57 adjusts parameters of the machine learning model, for example, through back propagation (back error propagation method). The machine learning model is, for example, a deep neural network (DNN) using a convolution neural network (CNN). Further, the machine learning model may set a weighting for each piece of learning data such that newer learning data is more easily reflected in an output.

The learning function 57 ends processing when back propagation has been performed on a predetermined number of sets of learning data and teacher data corresponding thereto. A machine learning model at that time is stored as a trained model 41-6. Further, the learning function 57 may generate a trained model 41-6 using physical characteristics data of a certain examination subject, information about an imaging target portion, and position information of the top board 33 during the imaging.

Meanwhile, a rate limiter may be provided in the learning function 57 to limit a difference between learning data and learning data 1 cycle before the learning data to a predetermined value or less.

Figures 7, 8:
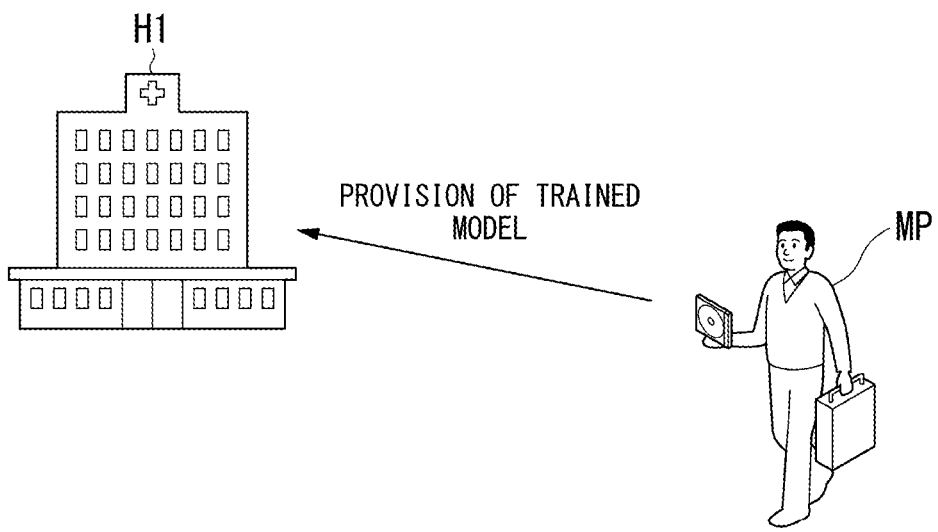
FIG. 7 is a diagram showing a look-up table of choices of physical characteristics data.
FIG. 8 is a diagram showing an environment in which an X-ray CT apparatus is used.

FIG. 7 is a diagram showing a look-up table of choices of physical characteristics data. It is possible to provide choices set in advance as shown in FIG. 7 and select physical characteristics data therefrom by an operator instead of inputting estimated values. In the look-up table, for example, choices such as "teenager" and "twenty" may be provided as ages and choices such as "tall," "normal" and "short" may be provided as heights. In addition, in the look-up table, choices indicating an average weight (55 to 70 [kg] in FIG. 7), weights equal to or greater than the average weight (70 [kg] or more in FIG. 7) and weights equal to or less than the average weight (55 [kg] or less in FIG. 7) may be provided as weights and choices suggesting weights such as "normal," "slightly obese" and "obese" may be provided. The X-ray CT apparatus 1 allows the operator to select any of choices of the look-up table such that the operator can alleviate a labor in measurement and input of correct values.

Meanwhile, choices of the look-up table as shown in FIG. 7 may be assigned to the trained model 41-6 as labels of ages, sexes, heights, weights and the like of physical characteristics data.

Further, the trained model 41-6 used by the learning function 57 or learning data and teacher data used by the learning function 57 may be generated by another X-ray CT apparatus 1.

Figure 9:
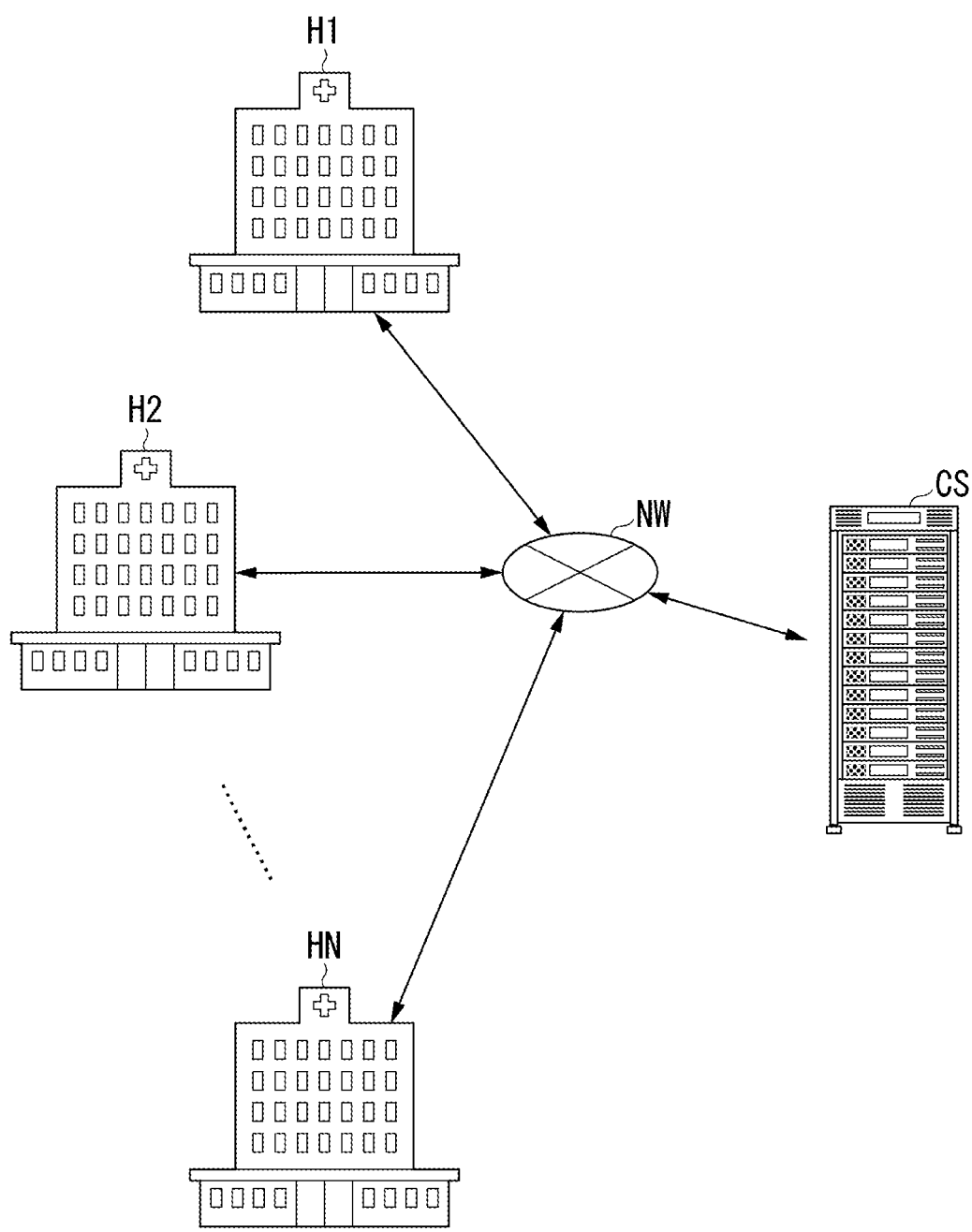
FIG. 9 is a diagram showing an environment in which an X-ray CT apparatus is used.

FIG. 8 and FIG. are diagrams describing environments in which the X-ray CT apparatus 1 is used. A trained model generated by another X-ray CT apparatus I or learning data and teacher data used by the learning function 57 are provided by a service representative MP or the like of the manufacturer of the X-ray CT apparatus 1 for a facility H1 using the X-ray CT apparatus 1 as shown in FIG. 8. Furthermore, a trained model generated by another X-ray CT apparatus 1 or learning data and teacher data used by the learning function 57 may be shared ay a plurality of facilities H1 to HN (N is any natural number) using the X-ray CP apparatuses 1 through a cloud server CS or the like via an external network NW, for example, as shown in FIG. 9. The cloud server CS may exclusively perform the same learning as the learning function 57. In addition, the trained model provided to the respective facilities H1 to HN in FIG. 9 may be provided by the manufacturer of the X-ray CT apparatus 1.

A data structure or a program serving as the trained model 41-6 may be stored as the trained model 41-6 in the memory 41 of the X-ray CT apparatus 1 when the X-ray CT apparatus is sold or installed as the trained model 41-6 in the memory 41 of the X-ray CT apparatus 1 after the X-ray CT apparatus 1 is sold. When a trained model 41-6 in which a imaging result of the X-ray CT apparatus 1 has been reflected has not been generated, for example, the learning function 57 may search trained models provided by the manufacturer or trained models provided by other facilities using the X-ray CT apparatus and allow the operator to determine whether to use a trained model that is a search result.

Figure 10:
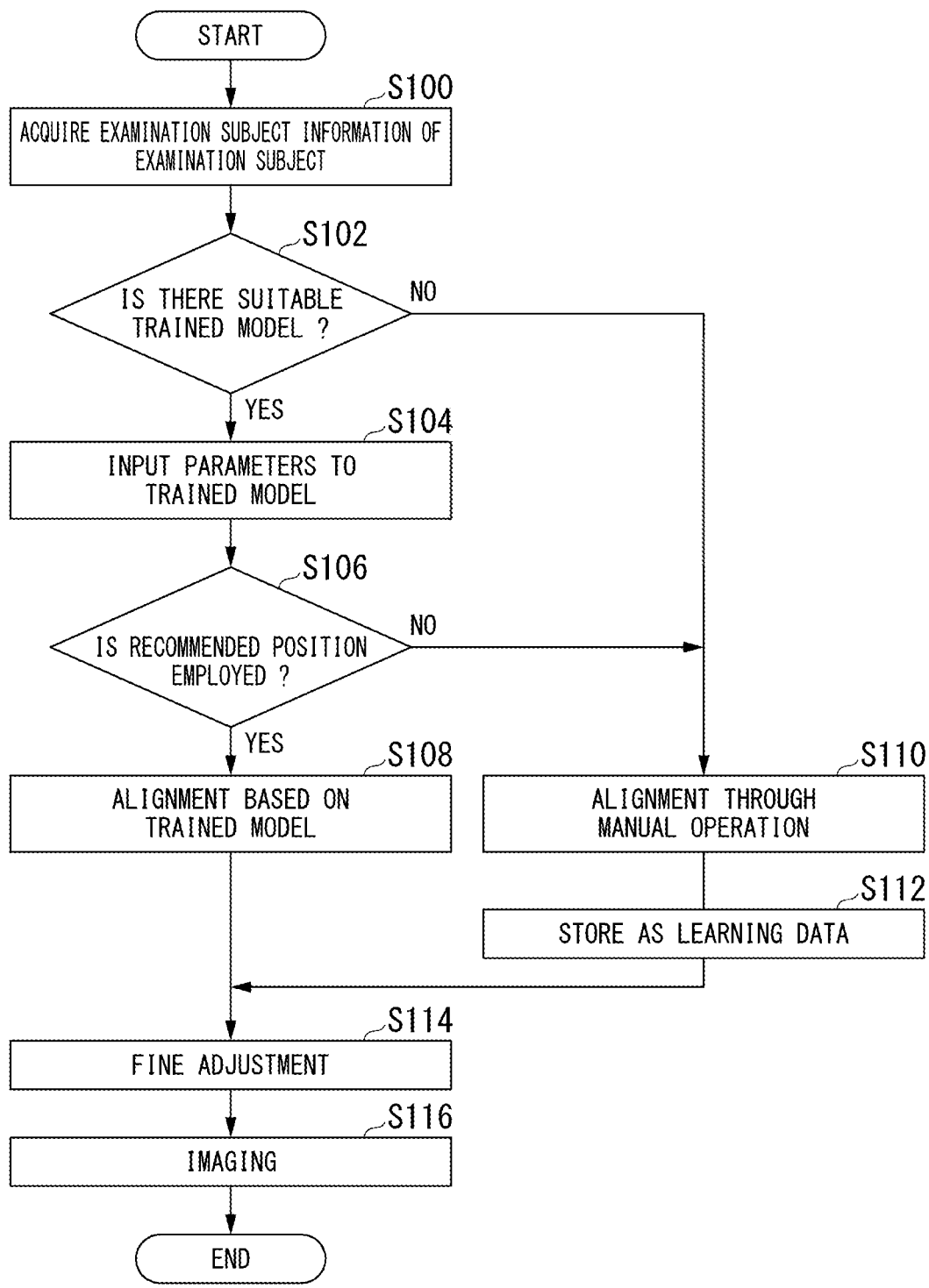
FIG. 10 is a flowchart showing an example of a flow of imaging processing performed by an X-ray CT apparatus.

FIG. 10 is a flowchart showing an example of a flow of imaging processing performed by the X-ray CT apparatus 1.

First, the examination subject information acquisition function 55-1 acquires physical characteristics data of the examination subject P and information about an imaging target portion stored in the examination subject information 41-1 (step S100). Next, the automatic alignment function 55-2 determines whether there is a trained model 41-6 suitable for the examination subject P (step S102). When it is determined that there is a suitable trained model 41-6, the automatic alignment function 55-2 applies the physical characteristics data and the information about the imaging target portion that are input parameters to the trained model (step S104) and receives an input of a result of determination of an operator with respect to whether to move the top board 33 to a recommended position output as a result of application of the data and information to the trained model (step S106). Further, if there is a plurality of trained models 41-6 selected in step S102, presence of a plurality of choices may be displayed on the display 42 such that the operator selects a trained model in step S104 or a most suitable trained model 41-6 may be automatically selected in step S104.

When it is determined that an input of the operator which indicates movement of the top board 33 to the recommended position has been received in step S106, the automatic alignment function 55-2 moves the top board 33 to the recommended position (step S108). When it is determined that an input of the operator which indicates movement of the top board 33 to the recommended position has not been received in step S106, that is, when it is determined that an input indicating manual alignment has been received or when it is not determined that there is a suitable trained model 41-6 by the automatic alignment function 55-2 in step S102, the manual alignment function 55-3 receives an input of alignment by the operator and moves the top board 33 (step S110). Subsequently, the learning function 57 stores an alignment result in step 110 as learning data (step 112).

The manual alignment function 55-3 receives an input operation of finely adjusting a final position of the top board 33 after step S110 or processing of step S108 performed by the automatic alignment function 55-2 (step S114). Subsequently, the scan execution function 55-4 performs imaging (step S116). Hereby, description of processing of this flowchart ends. Meanwhile, the above-described step S112 may be performed after the processing of step S108.

Figure 11:
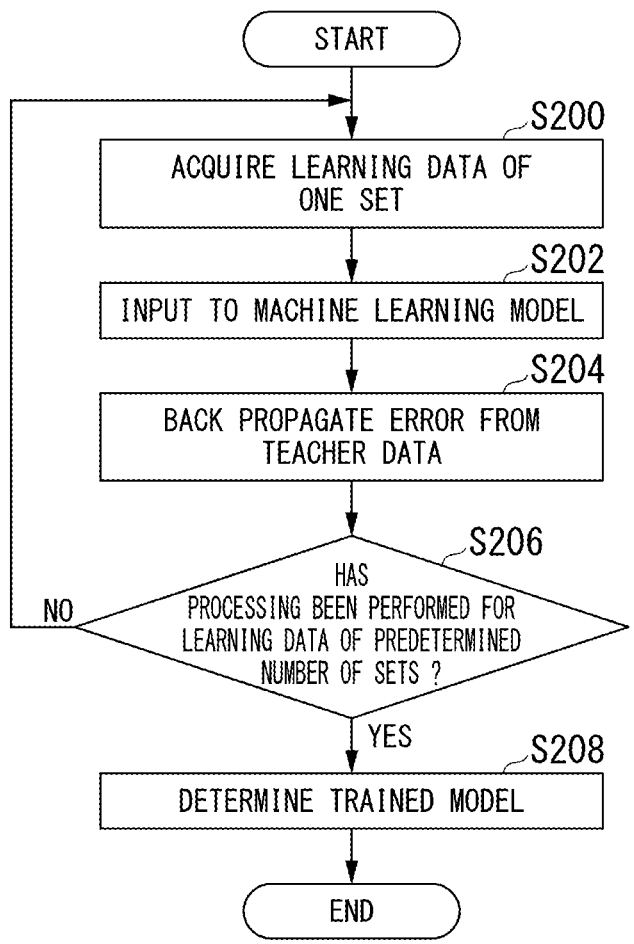
FIG. 11 is a flowchart showing an example of a flow of learning processing performed by a learning function.

FIG. 11 is a flow chart showing an example of a flow of learning processing performed by the learning function 57. The flow chart of FIG. 11 may be performed whenever the X-ray CT apparatus 1 ends imaging of one examination subject or when the amount of learning data stored in step S112 of FIG. 10 is equal to or greater than a predetermined number of sets as a result of alignment through the aforementioned manual operation performed by the operator.

First, the learning function 57 acquires learning data of one set (step S200). Subsequently, the learning function 57 inputs the learning data of one set acquired in step S200 to a machine learning model (step S202) and back propagates an error from teacher data corresponding to the learning data of one set (step S204).

Subsequently, the learning function 57 determines processing of step S202 and processing of step S204 have been performed for learning data of a predetermined number of sets (step S206). When processing of step S202 and processing of step S204 have not been performed for learning data of the predetermined number of sets, the learning function 57 returns to processing of step S200. When processing of step S202 and processing of step S204 have been performed for learning data of the predetermined number of sets, the learning function 57 determines a trained model 41-6 using parameters at that time (step S208) and ends processing of this flowchart.

Here, an image diagnostic apparatus of a reference example will be described. FIG. 12 is a diagram showing a problem occurring in the image diagnostic apparatus of the reference example. The image diagnostic apparatus of the reference example does not include a function of performing alignment on the basis of physical characteristics data of an examination subject and information about an imaging target portion as in the X-ray CT apparatus 1 of the embodiment.

For example, when a imaging center (an axis during imaging) SL is automatically set at an average position with respect to information such as the height and weight of an examination subject P, the sex and the age of the examination subject P during imaging of a sectional image of the examination subject P, there is a case in which an FOV center deviates due to the body type of the examination subject P and thus setting of the imaging center is inappropriate When the abdomen of the examination subject P has inflated due to ascites or the like, as shown in FIG. 12, overflow artifacts are highly likely to be detected at positions indicated by positions O1 and O2 in a CT image. In view of this, the X-ray CT apparatus 1 of the embodiment performs alignment on the basis of physical characteristics data of an examination subject and information about an imaging target portion including an artifact factor, as described above, and thus can prevent occurrence of such a problem.

According to the above-described X-ray CT apparatus 1 of the first embodiment, it is possible to efficiently perform operations such as alignment of an examination subject P before imaging by including the automatic alignment function 55-2 which outputs a recommended position of the top board 33 by inputting to the trained model 41-6, the examination subject information 41-1 including physical characteristics data of the examination subject and information atom an imaging target portion acquired by the examination subject information acquisition function 55-1.

Second Embodiment

Hereinafter, a nuclear medical diagnostic apparatus 2 of a second embodiment will be described. Meanwhile, in the description below, components and functions the same as those in the first embodiment are denoted by the same reference signs and detailed description thereof will be omitted. Furthermore, "A" is attached to reference signs of components or functions different from those in the first embodiment while having the same names as those in the first embodiment.

Figure 13:
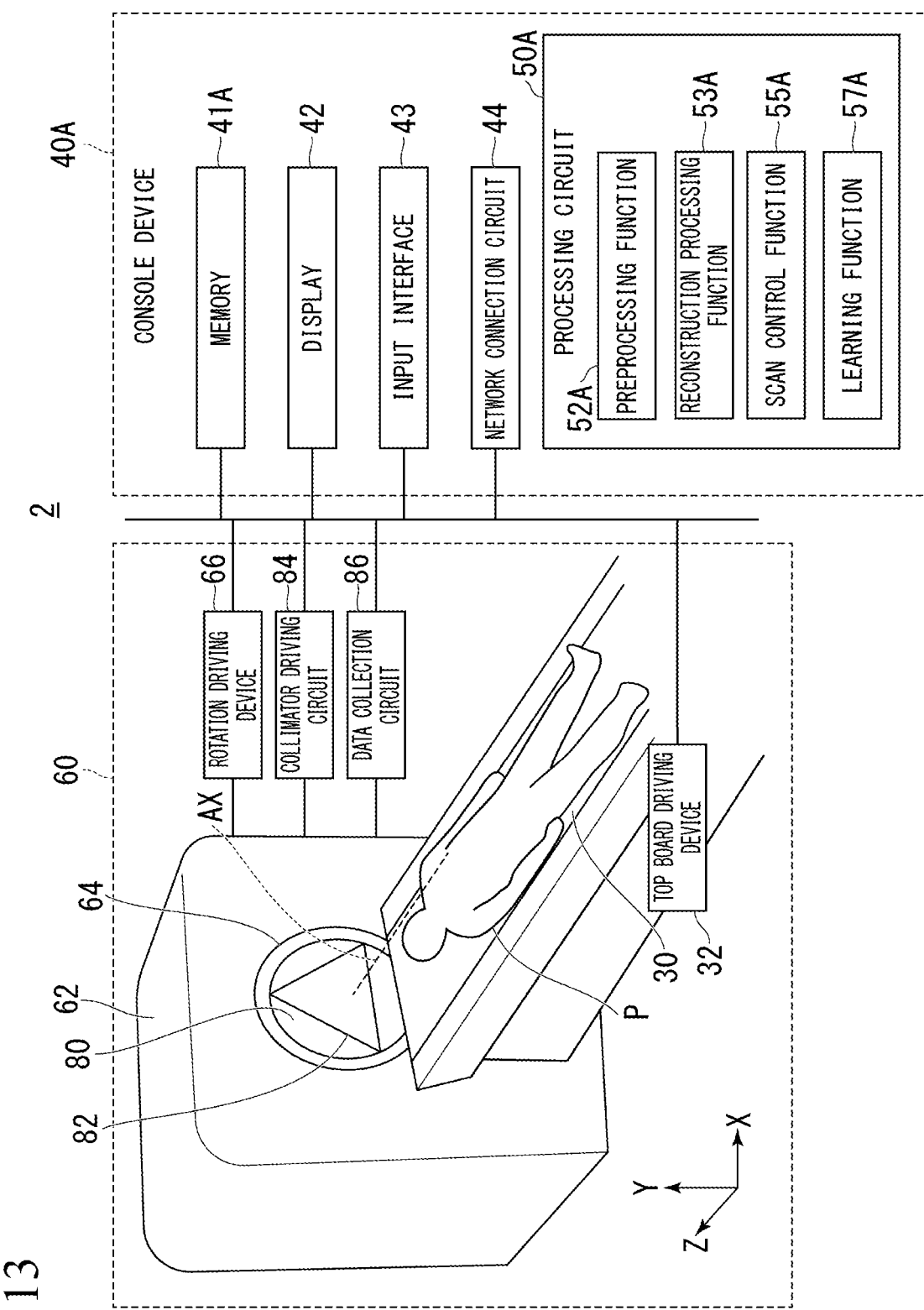
FIG. 13 is a configuration diagram of a nuclear medical diagnostic apparatus according to a second embodiment.

FIG. 13 is a configuration diagram of the nuclear medical diagnostic apparatus 2 according to the second embodiment. The nuclear medical diagnostic apparatus 2 includes, for example, a scanner device 60 and a console device 40A. In the second embodiment, the console device 40A is an example of a medical image diagnostic apparatus.

[Scanner Device]

The scanner device 60 includes, for example, a fixed holder 62, a rotary holder 64, a rotation driving device 66, three gamma ray detectors 80 and collimators 82 attached to the rotary holder 64 while being shifted by 120 degrees, a collimator driving circuit 84, a data collection circuit 86 and a bed device 30.

The fixed holder 62 is fixed to the floor of a room in which the scanner device 60 is installed. The rotary holder 64 is supported such that it can rotate around a rotation axis AX with respect to the fixed holder 62. The examination subject P is placed on the top board 33 such that the body axis thereof is appropriately parallel to the rotation axis AX of the rotary holder 64.

The rotation driving device 66 rotates the rotary holder 64 on the rotation axis AX. The rotation driving device 66 includes, for example, a driving means such as a motor, an electronic component for controlling the driving means, and a transfer means such as a roller which transfers rotary power of a rotation axis of the driving means to the rotary holder 64. The rotation driving device 66 is controlled by a processing circuit 50A. For example, the processing circuit 50A can collect projection data of the examination subject P from a plurality of directions by rotating the gamma ray detectors 80 on the rotation axis AX through the rotary holder 64 continuously or by stages.

The gamma ray detectors 80 detect gamma rays radiated from RI (radioactive isotope) such as technetium administered to the examination subject P. Detection timing of the gamma ray detectors 80 is controlled by the processing circuit 50A. For example, the gamma ray detectors 80 may be scintillator type detectors or semiconductor type detectors. This will be described later.

The collimators 82 control incident angles of gamma rays input to the gamma ray detectors 80. The collimators 82 are formed of a material through which radioactive rays hardly pass, such as lead or tungsten. A plurality of holes for controlling a direction in which photons move are provided in the collimators 82. The cross section of these holes may have a polygonal shape such as a hexagon, for example.

When the gamma ray detectors 80 are scintillator type detectors, each gamma ray detector 80 includes, for example, a scintillator which emits momentary flash when gamma rays collimated by the collimator 82 are input, a light guide, a plurality of photoelectron multipliers which are two-dimensionally arranged and detect light emitted from the scintillator, and an electronic circuit for a scintillator. The scintillator is composed of, for example, thallium-activated sodium iodide NaI(Tl). The electronic circuit for a scintillator generates incident position information (position information), incident intensity information and incident time information of gamma rays within a detection plane formed by the plurality of photoelectron multipliers on the basis of outputs of the plurality of photoelectron multipliers and outputs the generated information to the processing circuit 50A of the console device 40A whenever a gamma ray input event occurs. The position information may be two-dimensional coordinate information within the detection plane or information indicating a primary cell to which gamma rays have been input from among a plurality of divided regions (primary cells) obtained by virtually dividing the detection plane in advance (for example, dividing the detection plane into 1024×1024 cells).

When the gamma ray detectors 80 are semiconductor type detectors, each gamma ray detector 80 includes, for example, a plurality of semiconductor elements two-dimensionally arranged to detect gamma rays collimated by the collimator 82, an electronic circuit for a semiconductor, and the like. The semiconductor elements are formed of, for example, CdTe or CdZnTe (CZT). The electronic circuit for a semiconductor generates incident position information, incident intensity information and incident time information on the basis of outputs of the semiconductor elements and outputs the generated information to the processing circuit 50A whenever a gamma ray input event occurs. This position information is information indicating a semiconductor element to which gamma rays have been input from among a plurality of semiconductor elements (e.g., 1024×1024 semiconductor elements).

The collimator driving circuit 84 drives the gamma ray detectors 80 and the collimators 82 in a direction in which they approach or become fat away from the rotation axis AX of the rotary holder 64, for example.

The data collection circuit 86 includes, for example, a printed circuit board. The data collection circuit 86 executes imaging of the examination subject P by controlling at least the gamma ray detectors 80 according to an instruction from the processing circuit 50A. The data collection circuit 86 collects detection position information and intensity information of gamma rays detected by the gamma ray detectors 80, information representing relative positions of the gamma ray detectors 80 and the examination subject P, and a gamma ray detection lime by associating them with a gamma ray input event.

The data collection circuit 86 reconstructs two-dimensional images acquired as imaging results of the gamma ray detectors 80 and generates a cross-sectional image (three-dimensional image is also possible) through which a distribution and a movement process of radiopharmaceuticals are detected.

The top board 33 mounts the examination subject P thereon and controls motions of the examination subject P. The bed driving device 32 is controlled by the processing circuit 50A to move the top board 33 along the rotation axis AX of the rotary holder 64 or in a vertical direction (Y direction in the figure).

[Console Device]

The console device 40A may be a dev ice designed exclusively for the nuclear medical diagnostic apparatus 2 or a device in which a program necessary for general-purpose personal computers and workstations has been installed. In the former case, some components of the console device 40A may be distributed to the fixed holder 62 and disposed therein.

Figure 14:
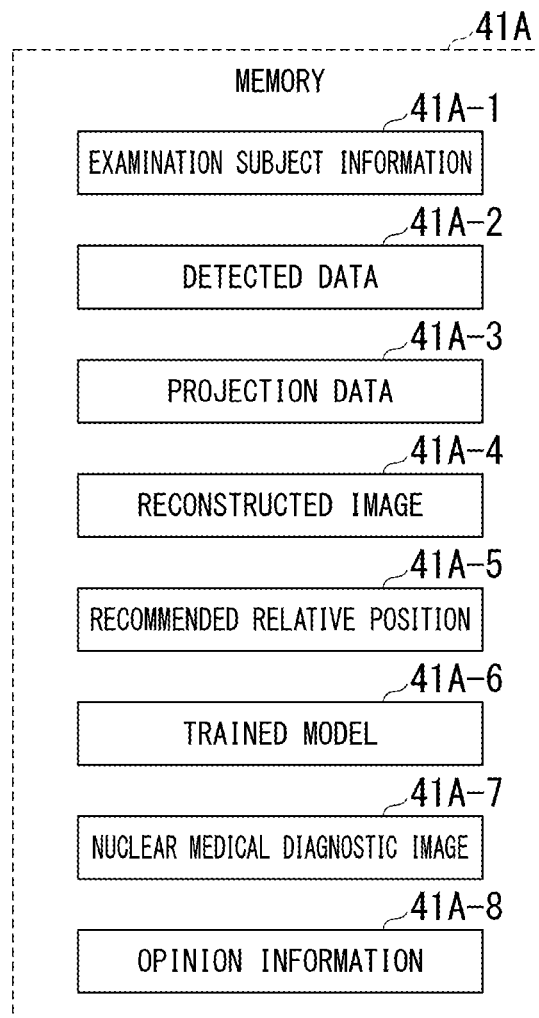
FIG. 14 is a diagram showing an example of data stored in a memory.

FIG. 14 is a diagram showing an example of data stored in a memory 41A. The memory 41A stores, for example, information such as examination subject information 41A-1, detected data 41A-2, projection data 41A-3, reconstructed images 41A-4, recommended relative positions 41A-5, trained models 41A-6, and nuclear medical diagnostic images 41A-7 and opinion information 41A-8 generated by the processing circuit 50A. In addition, the memory 41A may store programs executed by a hardware processor of the processing circuit 50A.

The processing circuit 50A includes, for example, a preprocessing function 52A, a reconstruction processing function 53A, a scan control function 55A, and a learning function 57A. The processing circuit 50A realizes these functions, for example, by the hardware processor executing programs stored in the processing circuit 50A.

The preprocessing function 52A executes preprocessing on the projection data 41A-3 acquired by the scan control function 55A which will be described later, for example, on the basis of preprocessing condition information received through the input interface 43 or stored in the memory 41A. Preprocessing includes, for example, uniformity correction processing, rotation center correction processing, preprocessing filter processing, processing of converting fan beam projection data into parallel beam projection data, and the like.

The reconstruction processing function 53A performs reconstruction processing on projection data on which preprocessing has been performed by the preprocessing function 52A to generate volume data. The volume data is stored in the memory 41A as one of nuclear medical diagnostic images 41A-7. The reconstruction processing function 53A performs reconstruction processing, for example, on the basis of Chang iterative approximation method (Iterative Chang). Instead of this, the reconstruction processing function 53A may perform reconstruction processing on the basis of maximum likelihood-expectation maximization (ML-EM), ordered subset expectation maximization (OS-EM) and the like.

The scan control function 55A controls some or all of the rotation driving device 66, the collimator driving circuit 84, the data collection circuit 86 and the bed device 30 on the basis of a scan plan execution instruction received through the input interface 43 to execute scanning and generates the projection data 41A-3 from the data collection circuit 86.

The learning function 57A stores information about relative positions of the gamma ray detectors 80 and the bed device 30 immediately before imaging is started and during imaging and information representing relative positions of the gamma ray detectors 80 and the examination subject P as recommended relative positions 41A-5 in addition to recommended positions of the top board 33. The recommended relative positions 41A-5 include, for example, information about relative positions of the gamma ray detectors 80 and the bed device 30 immediately before imaging is started and information representing relative positions of the gamma ray detectors 80 and the examination subject P (a direction in which the gamma ray detectors 80 approach the examination subject P, a distance by which the gamma ray detectors 80 approach the examination subject P, and the like), or absolute driving quantities of the gamma ray detectors 80 and the like for realizing the same. In the description below, information included in the recommended relative positions 41A-5 may be simply referred to as "recommended relative positions." Information included in the recommended relative positions 41A-5 is an example of "relative position information".

An automatic alignment function 55A-2 selects a trained model 41A-6 depending on the examination subject P and sets a recommended relative position on the basis of an output result obtained by inputting, to the selected trained model 41A-6, physical characteristics data and information about a imaging target portion of examination subject information 41A-1 of the examination subject P output from an examination subject information acquisition function 55A-1.

The trained model 41A-6 outputs a recommended relative position on the basis of the physical characteristics data of the examination subject P and information about an imaging target portion. The trained model 41A-6 outputs relative coordinates that should be a feature point of the examination subject P immediately before scan imaging is started in addition to the height of the top board 33 as a recommended relative position of the bed device 30. Meanwhile, when a headrest, a fixture or the like is provided at a specific position on the bed dev ice 30 and the position of the examination subject P on the bed device 30 barely changes in each examination (an error can be ignored), any portion of the top board 33 may be used tor alignment of a recommended relative position.

Figure 15:
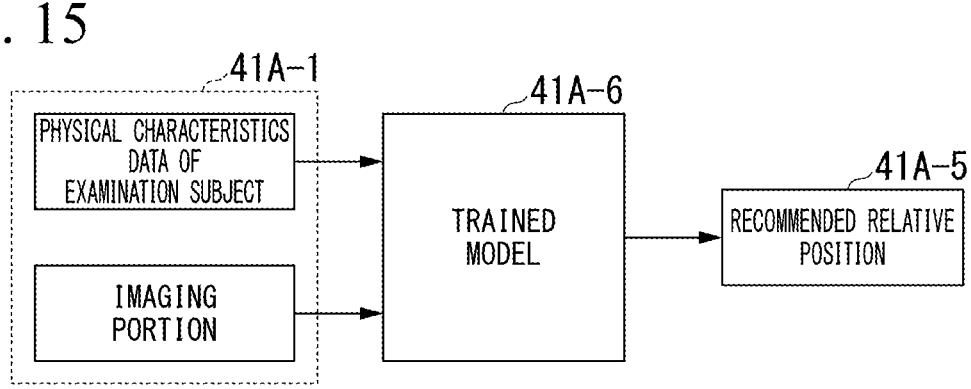
FIG. 15 is a diagram showing output processing performed by a trained model.

FIG. 15 is a diagram showing output processing performed by the trained model 41A-6. The trained model 41A-6 outputs a recommended relative position of the recommended relative positions 41A-5 by receiving physical characteristics data of the examination subject P and information about an imaging target portion as parameters A manual alignment function 55A-3 receives an input of an operator of a medical image diagnostic apparatus 1A with respect to whether to employ a recommended relative position set by the automatic alignment function 55A-2. When an input of the operator which represents movement to the recommended relative position is received, the manual alignment function 55A-3 moves the rotary holder 64, the top board 33 (not shown) and at least parts of the gamma ray detectors 80 and the collimators 82 to the recommended relative position set by the automatic alignment function 55A-2 and then receives an operation of realignment or fine adjustment. In addition, when an input of the operator which represents that movement to the recommended relative position is not performed is received, the manual alignment function 55A-3 controls operations of the rotary holder 64, the top board 33 and at least parts of the gamma ray detectors 80 and the collimators 82 according to the input operation. The manual alignment function 55A-3 reflects results of realignment or fine adjustment in the recommended relative position 41A-5.

Figure 16:
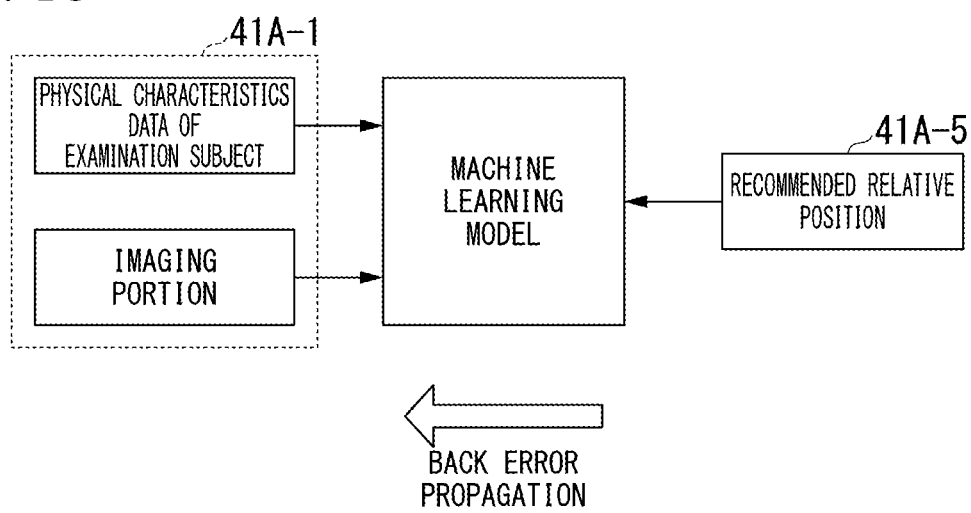
FIG. 16 is a diagram showing a trained model generation processing of a learning function.

FIG. 16 is a diagram showing trained model generation processing of the learning function 57A. For example, the learning function 57 generates a machine learning model for generating a trained model using physical characteristics data of a certain examination subject P and information about a imaging target portion included in the examination subject information 41-1 as learning data and using position information of the gamma ray detectors 80 and position information of the bed device 30 such as the top board 33 during imaging included in the recommended relative position 41A-5 as teacher data.

Figure 17:
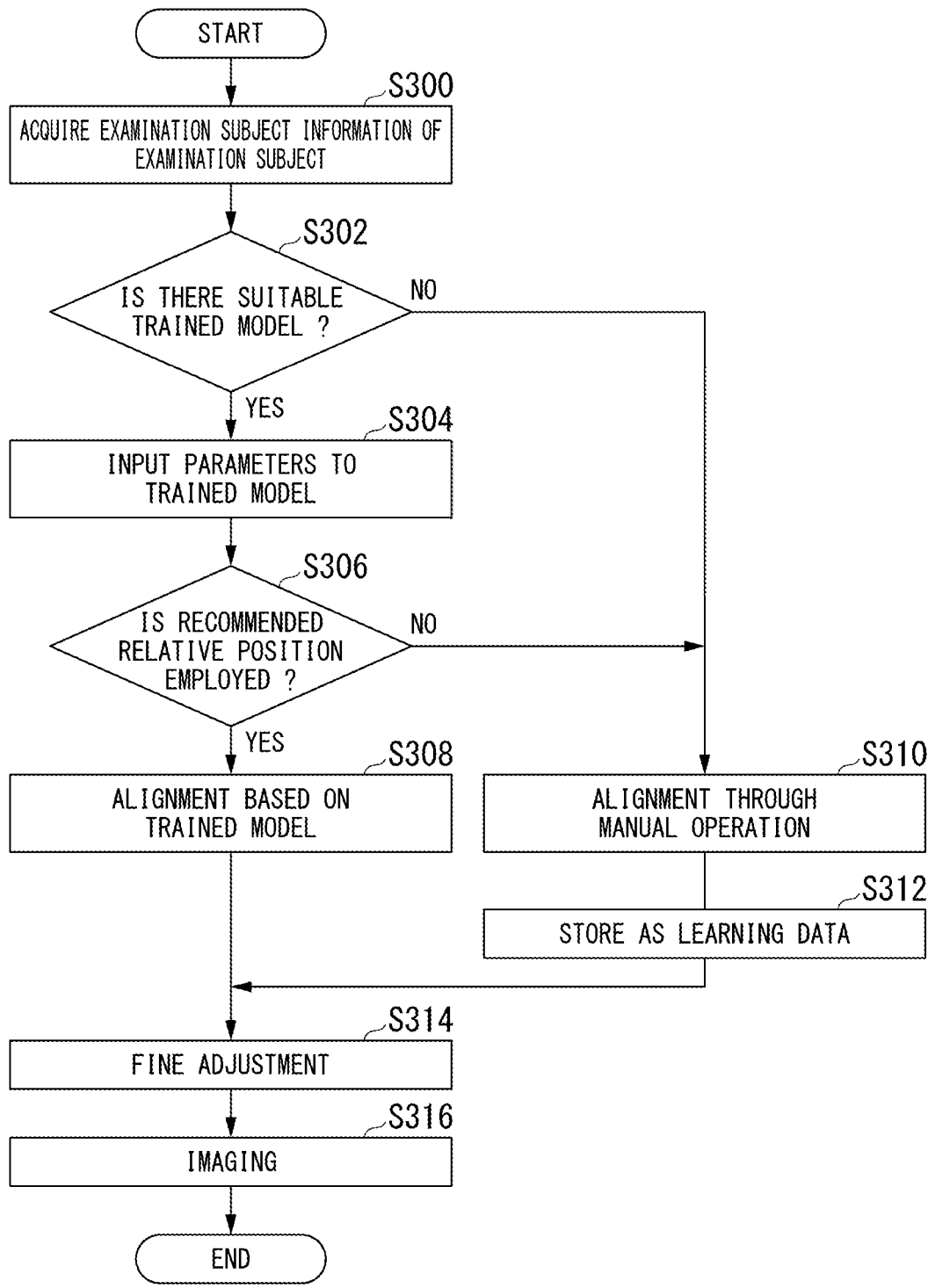
FIG. 17 is a flowchart showing an example of a flow of imaging processing performed by a nuclear medical diagnostic apparatus.

FIG. 17 is a flowchart showing an example of a flow of imaging processing performed by the nuclear medical diagnostic apparatus 2.

First, the examination subject information acquisition function 55A-1 acquires physical characteristics data of the examination subject P and information about an imaging target portion stored in the examination subject information 41A-1 (step S300). Subsequently, the automatic alignment function 55A-2 determines whether there is a trained model 41A-6 suitable for the examination subject P (step S302). A "suitable trained model 41A-6" may be selected depending on the physical characteristics data of the examination subject P as in the first embodiment. When it is determined that there is a trained model 41A-6 suitable for the examination subject P, the automatic alignment function 55A-2 applies the physical characteristics data and information about the imaging target portion which are input parameters to the trained model (step S304) and receives an input of a determination result of an operator with respect to whether to move the fixed holder 62, the rotary holder 64 and the bed device 30 to a recommended relative position output as a result of application of the physical characteristics data and the information about the imaging target portion (step S306). Meanwhile, when there is a plurality of trained models 41A-6 selected in step S302, presence of a plurality of choices may be displayed on the display 42 such that a choice of the operator is received in step S304 or a most suitable trained model 41A-6 may be selected in step S304.

When it is determined that an input of the operator which represents movement of the rotary holder 64 and the like to the recommended relative position has been received in step S306, the automatic alignment function 55A-2 moves the rotary holder 64 and the like to the recommended relative position (step S308). When it is determined that the input of the operator which represents movement of the rotary holder 64 and the like to the recommended relative position has not been received, that is, when it is determined that an input representing alignment through a manual operation has been received in step S306 or when the automatic alignment function 55A-2 does not determine that there is a suitable trained model 41A-6 in step S302, the manual alignment function 55A-3 receives an input of alignment performed by the operator and moves the rotary holder 64 and the like (step S310). Subsequently, the learning function 57A stores an alignment result according to step S310 as learning data (step S312).

The manual alignment function 55A-3 receives an input operation of finely adjusting final positions of the rotary holder 64 and the like (step S312) after processing of step S310 or step S308 performed by the automatic alignment function 55A-2. Subsequently, the scan execution function 55A-4 performs imaging (step S314). Hereby, description of processing of this flowchart ends. Meanwhile, the aforementioned step S312 may be performed after processing of step S308.

According to the console device 40A of the nuclear medical diagnostic apparatus 2 of the above-described second embodiment, it is possible to efficiently perform alignment of the bed device 30 during imaging and the gamma ray detectors 80 with the position of the examination subject P by including the automatic alignment function 55A-2 which outputs recommended relative positions including position information of the rotary holder 64, the top board 33 and at least parts of the gamma ray detectors 80 and the collimators 82 by inputting physical characteristics data and information about a imaging target portion of the examination subject information 41A-1 to a trained model 41A-6 which satisfies conditions of the examination subject P.

Third Embodiment

Figure 18:
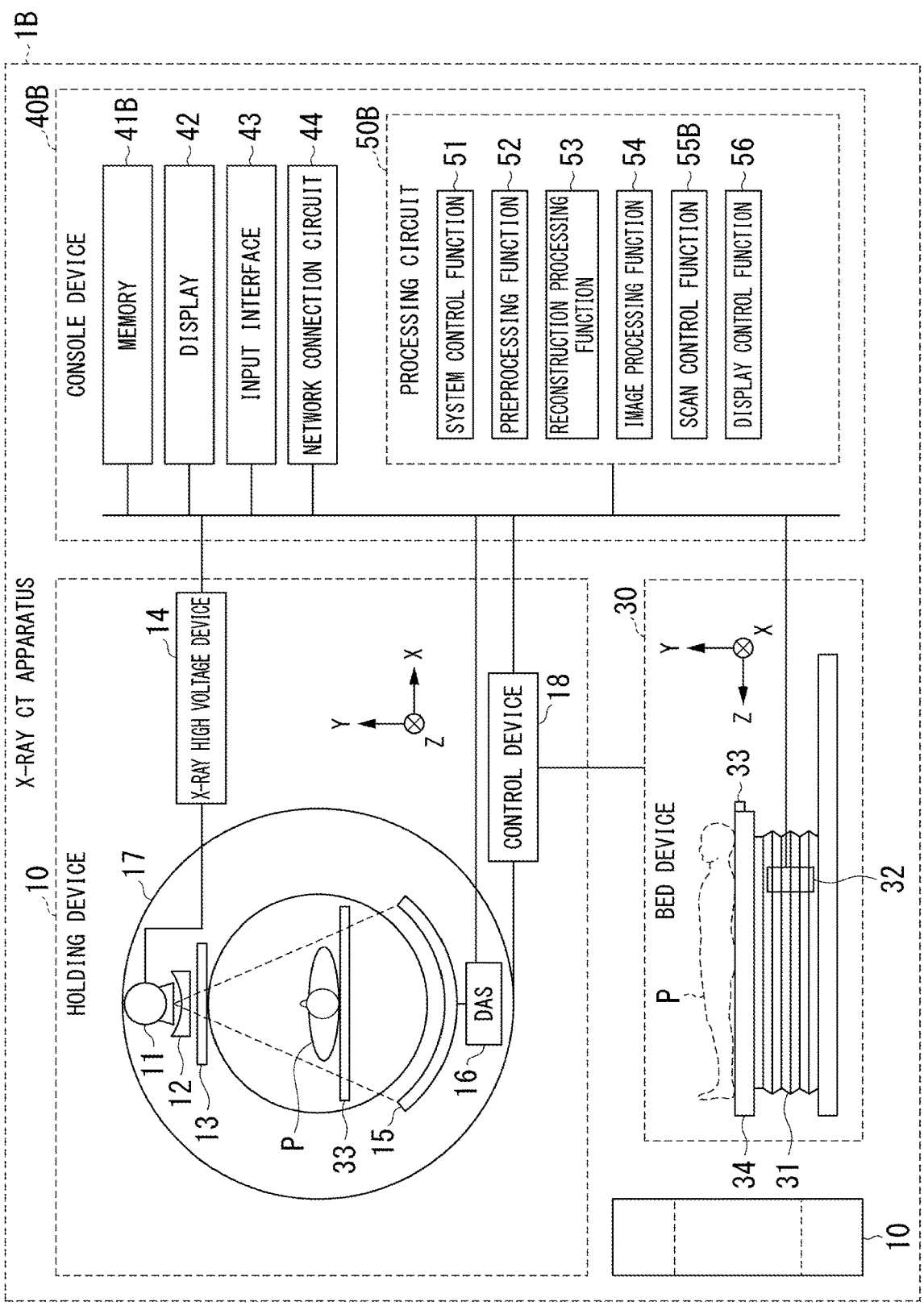
FIG. 18 is a configuration diagram of an X-ray CT apparatus according to a third embodiment.

FIG. 18 is configuration diagram of an X-ray CT apparatus 1B according to a third embodiment. Meanwhile, in the description below, components and functions the same as those in the first embodiment are denoted by the same reference signs and detailed description thereof will be omitted Furthermore, "B" is attached to reference signs of components or functions different from those in the first embodiment while having the same names as those in the first embodiment. The X-ray CT apparatus 1B differs from the X-ray CT apparatus 1 of the first embodiment in that it does not include the learning function 57.

Figure 19:
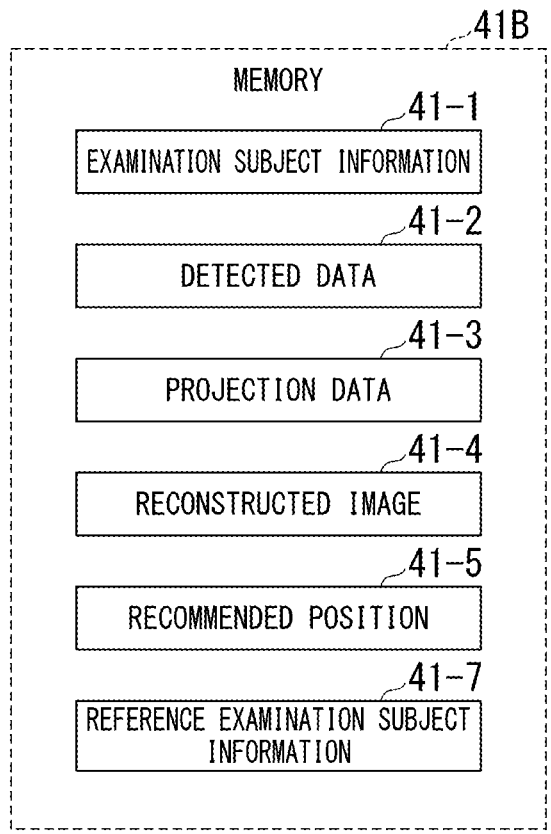
FIG. 19 is a diagram showing an example of data stored in a memory.

FIG. 19 is a diagram showing an example of data stored in a memory 41B. The memory 41B stores, for example, information of reference examination subject information 41-7 instead of trained models 41-6 of the memory 41 of the first embodiment. The reference examination subject information 41-7 includes examination subject information 41-1 including an examination subject different from the examination subject P, and position information of the top board 33 when the examination subject different from the examination subject P is imaged and is accumulated whenever imaging through the X-ray CT apparatus 1B is performed.

Figure 20:
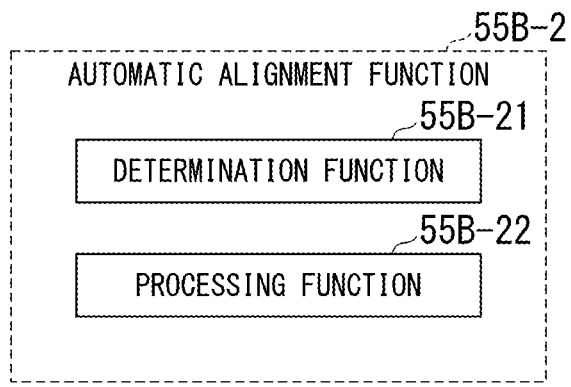
FIG. 20 is a configuration diagram of a scan control function.

FIG. 20 is a configuration diagram of an automatic alignment function 55B-2. The automatic alignment function 55B-2 includes, for example, a determination function 55B-21 and a processing function 55B-22.

The determination function 55B-21 searches the reference examination subject information 41-7 and determines a method for deriving a recommended position of the top board 33 in imaging of the examination subject P The determination function 55B-21 is an example of a "determination unit." The processing function 55B-22 assists alignment by setting a recommended position of the top board 33 in imaging of the examination subject P using a method for deriving a recommended position of the top board 33 determined by the determination function 55B-21. The processing function 55B-22 is an example of a "processing unit."

Recommended Position Derivation Method

An operator of the X-ray CT apparatus 1B sets a method for deriving a recommended position of the top board 33 before the examination subject P is imaged.

Methods for deriving a recommended position of the top board 33 include, for example, a method of using reference examination subject information 41-7 having imaging conditions most similar to those of the examination subject P as an employment condition as it is, method of using reference examination subject information 41-7 having a physique most similar to that of the examination subject P as an employment condition as it is, a method of using a simple average or a weighted average of a plurality of pieces of reference examination subject information 41-7 having imaging conditions similar to those of the examination subject P as an employment condition, a method of using a simple average or a weighted average of a plurality of pieces of reference examination subject information 41-7 having a physique similar to that of the examination subject P as an employment condition, a method of using a simple average or a weighted average of a plurality of pieces of reference examination subject information 41-7 having imaging conditions and a physique similar to those of the examination subject P as an employment condition, and the like.

Figure 21:
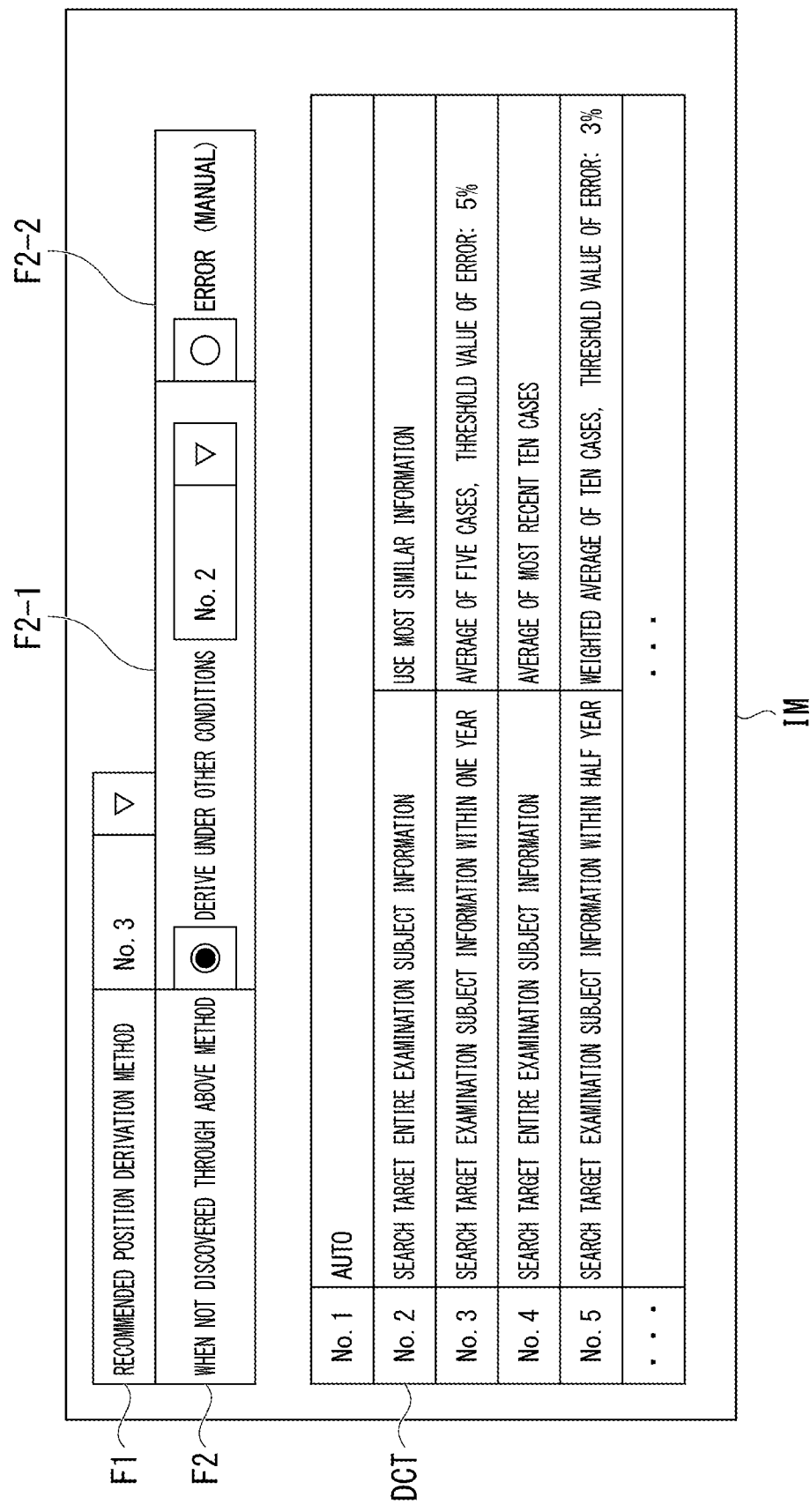
FIG. 21 is a diagram showing an example of recommended position setting conditions.

FIG. 21 is a diagram showing setting conditions for a recommended position 41-5. For example, the operator of the X-ray CT apparatus 1B may operate the input interface 43 with reference to an image IM displayed on the display 42 shown in FIG. 21 to set a method for deriving a recommended position. The image IM includes a condition table DCT for a method for deriving a recommended position of the top board 33, an input format F1 through which a derivation method to be used in the condition table DCT is set is received, an input format F2 through which processing setting when a recommended position of the top board 33 has not been derived through a derivation method designated through the input format F1 is received, and the like. The input format F2 includes an input format F2-1 through which an alternative method other than a derivation method set through the input format F1 is received and an input format F2-2 through which processing performed by the automatic alignment function 55B-2 is suspended and setting for promoting manual setting by the operator of the X-ray CT apparatus 1B is received.

The condition table DCT includes a plurality of methods for deriving a recommended position of the top board 33 which have different calculation methods and different number of pieces of reference examination subject information 41-7 that are calculation targets. With respect to derivation methods included in the condition table DCT, customized input by the operator of the X-ray CT apparatus 1B may be possible. Further, when a derivation method employing a weighted average of a plurality of pieces of reference examination subject information 41-7 having imaging conditions and the like similar to those of the examination subject P is set, the operator of the X-ray CT apparatus 1B may personally set a degree of weighting performed on a detection value from among the examination subject information 41-1 in the condition table DCT Meanwhile, the determination function 55B-21 may search the reference examination subject information 41-7, select any derivation method from the condition table DCT depending on a search result and determine the selected derivation method. Imaging conditions include conditions such as information about a imaging target portion of the examination subject P (e.g., a chest, a head, or the like), an insertion direction representing whether the examination subject P will be inserted into the holding device 10 head first (HF) or foot first (FF), whether angiography will be performed, and a posture of the examination subject P.

FIG. 22 is a diagram showing processing of the processing function 55B-22. The reference examination subject information 41-7 includes a plurality of pieces of physical characteristics data of examination subjects and position information (e.g., coordinates and the like) of the top board 33 during imaging as shown.

When a derivation method determined by the determination function 55B-21 is a derivation method which selects a top board position based on physical characteristics data of an examination subject most similar to the physical characteristics data of the examination subject P as a recommended position and employs it, the processing function 55B-22 outputs, as a recommended position of the examination subject P, a top board position of reference examination subject information 41-7 of another examination subject having the same imaging condition as those of the examination subject P and a degree of physical characteristics data matching that of the examination subject P which is equal to or greater than a predetermined degree. The processing function 55B-22 sets, as a recommended position, for example, position information of the top board 33 of an examination subject F having physical characteristics data (sex, height, age, weight and body fat percentage) most similar to that of the examination subject P from among the reference examination subject information 41-7 in the figure.

When the derivation method determined by the determination function 55B-21 is a derivation method which derives a top board position based on physical characteristics data of reference examination subject information 41-7 having the same imaging conditions as those of the examination subject P as a recommended position, the processing function 55B-22 derives an average of top board positions of examination subjects A to E and sets the average as a recommended position of the examination subject P.

When a derivation method determined by the determination function 55B-21 is a derivation method employing a bed position based on physical characteristics data of an examination subject having physical characteristics data and imaging conditions most similar to those of the examination subject P, the processing function 55B-22 outputs, as a bed position information of the examination subject P, a bed position of reference examination subject information 41-7 of another examination subject having the same imaging conditions as those of the examination subject P and a degree of physical characteristics data and imaging condition matching those of the examination subject P which is equal to or greater than a predetermined degree. The processing function 55B-22 sets, as a recommended position, for example, position information of the top board 33 of an examination subject A having physical characteristics data (sex, height, age, weight and body fat percentage) and imaging conditions (e.g., contrast radiography and HF/FF) most similar to those of the examination subject P from among the reference examination subject information 41-7 in the figure.

When a derivation method determined by the determination function 55B-21 is a derivation method which selects and employs a bed position based on physical characteristics data of one or mom other examination subjects other than the examination subjects, the processing function 55B-22 outputs, as bed position information of the examination subject, bed position information of another examination subject having, a derivation condition closest to that of the examination subject P from among other examination subjects having the same imaging conditions as those of the examination subject P and degrees of physical characteristics data matching that of the examination subject P which is equal to or greater than a predetermined degree.

When the derivation condition is defined, for example, as a condition that an error between physical characteristics data of the examination subject P and physical characteristics data of another examination subject included in the reference examination subject information 41-7 is less than a predetermined threshold value, the determination function 55B-21 extracts reference examination subject information 41-7 having an error less than the predetermined threshold value and then derives a bed position from the extraction result.

For example, when the operator of the X-ray CT apparatus 1B sets a height error of less than 5[%] as a predetermined threshold value, the determination function 55B-21 determines that reference examination subject information 41-7 of an examination subject B will not be employed because the height of the examination subject B and the height of the examination subject P has an error therebetween which is equal to or greater than the predetermined threshold value. In this case, the processing function 55B-22 outputs, for example, a simple average (or a weighted average) of bed position information of examination subject A and examination subjects C and E having the same imaging conditions as those of the examination subject P as bed position information of the examination subject P.

In addition, when the operator of the X-ray CT apparatus 1B sets an age error of less than 5 [years] as a predetermined threshold value, the determination function 55B-21 determines that reference examination subject information 41-7 of the examination subject C will not be employed because the age of the examination subject C and the age of the examination subject P has an error therebetween which is equal to or greater than the predetermined threshold value In this case, the processing function 55B-22 outputs, for example, a simple average (or a weighted average) of bed position information of the examination subjects A and B and examination subjects D and E having the same imaging conditions as those of the examination subject P as bed position information of the examination subject P.

Furthermore, when the operator of the X-ray CT apparatus 1B sets a weight error of less than 3 [kg] as a predetermined threshold value, the determination function 55B-21 determines that reference examination subject information 41-7 of the examination subject D will not be employed because the weight of the examination subject D and the weight of the examination subject P has an error therebetween which is equal to or greater than the predetermined threshold value. In this case, the processing function 55B-22 outputs, for example, a simple average (or a weighted average) of bed position information of the examination subjects A to C and the examination subject E having the same imaging conditions as those of the examination subject P as bed position information of the examination subject P.

Further, when the operator of the X-ray CT apparatus 1B sets a body fat percentage error of less than 3[%] as a predetermined threshold value, the determination function 55B-21 determines that reference examination subject information 41-7 of the examination subject K will not be employed because the body fat percentage of the examination subject E and the body fat percentage of the examination subject P has an error therebetween which is equal to or greater than the predetermined threshold value. In this case, the processing function 55B-22 outputs, for example, a simple average (or a weighted average) of bed position information of the examination subjects A to D having the same imaging conditions as those of the examination subject P as bed position information of the examination subject P.

In addition, the operator of the X-ray CT apparatus 1B may set predetermined threshold values for a plurality of pieces of physical characteristics data. For example, when the operator of the X-ray CT apparatus 1B sets a height error of less than 5[%] and an age error of less than 5 [years] as predetermined threshold values, it is determined that reference examination subject information 41-7 of the examination subjects B and C will not be employed. In this case, the processing function 55B-22 outputs, for example, a simple average (or a weighted average) of bed position information of the examination subjects D and E having the same imaging conditions as those of the examination subject P as bed position information of the examination subject P.

The fact that an error between the physical characteristics data of the examination subject P and physical characteristics data of another examination subject included in reference examination subject information 41-7 is less than a predetermined value may be defined by a specific numerical value, defined using the look-up table of FIG. 7 (a range in which the same choices are set, a range in which neighboring choices are set, and the like in the look-up table), or defined by a statistical reliability section or the like.

When the operator of the X-ray CT apparatus 1B sets the same imaging conditions as a predetermined threshold value, the determination function 55B-21 determines that reference examination subject information 41-7 of examination subjects F and G will not be employed because the examination subject F with contrast radiography and the examination subject G with an insertion direction of FF have different imaging conditions.

In addition, when the examination subject information 41-1 includes a test purpose and precaution information of the examination subject P, the determination function 55B-21 may extract reference examination subject information 41-7 on the basis of the test purpose and the precaution information of the examination subject P. For example, when the examination subject information 41-1 includes precaution information of "presence of abdominal inflation," the determination function 55B-21 preferentially extracts reference examination subject information 41-7 including the precaution information of "presence of abdominal inflation."

Figure 23:
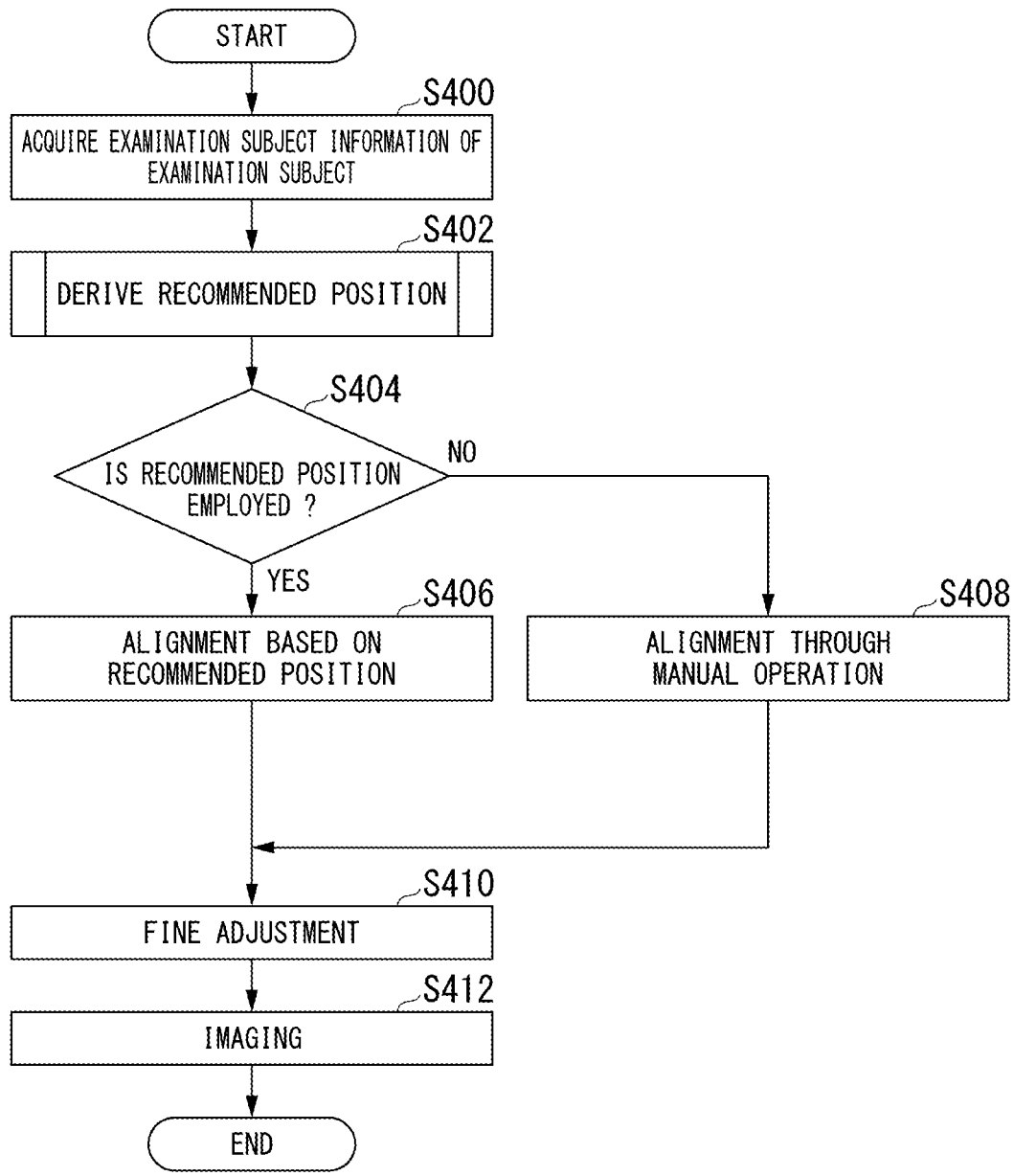
FIG. 23 is a flowchart showing an example of a flow of imaging processing performed by an X-ray CT apparatus.

FIG. 23 is a flowchart showing an example of a flow of imaging processing performed by the X-ray CT apparatus 1B.

First, the examination subject information acquisition function 55-1 acquires physical characteristics data of the examination subject P and information about an imaging target portion recorded in the examination subject information 41-1 (step S400). Then, the automatic alignment function 55B-2 derives a recommended position (step S402). Processing of step S402 will be described later. Subsequently, the automatic alignment function 55B-2 receives an input of a determination result from an operator with respect to whether to employ the recommended position (step S404).

The automatic alignment function 55B-2 moves the top board 33 to the recommended position when it is determined that an input of the operator which represents movement of the top board 33 to the recommended position has been received (step S406). When it is determined that an input of the operator which represents movement of the top board 33 to the recommended position has not been received, the manual alignment function 55-3 receives an input of alignment from the operator and moves the top board 33 (step S408).

The manual alignment function 55-3 receives an input operation of finely adjusting a final position of the top board 33 after processing of step S406 or step S408 (step S410). Then, the scan execution function 55-4 performs imaging (step S412). Hereby, description of processing of this flowchart ends.

Figure 24:
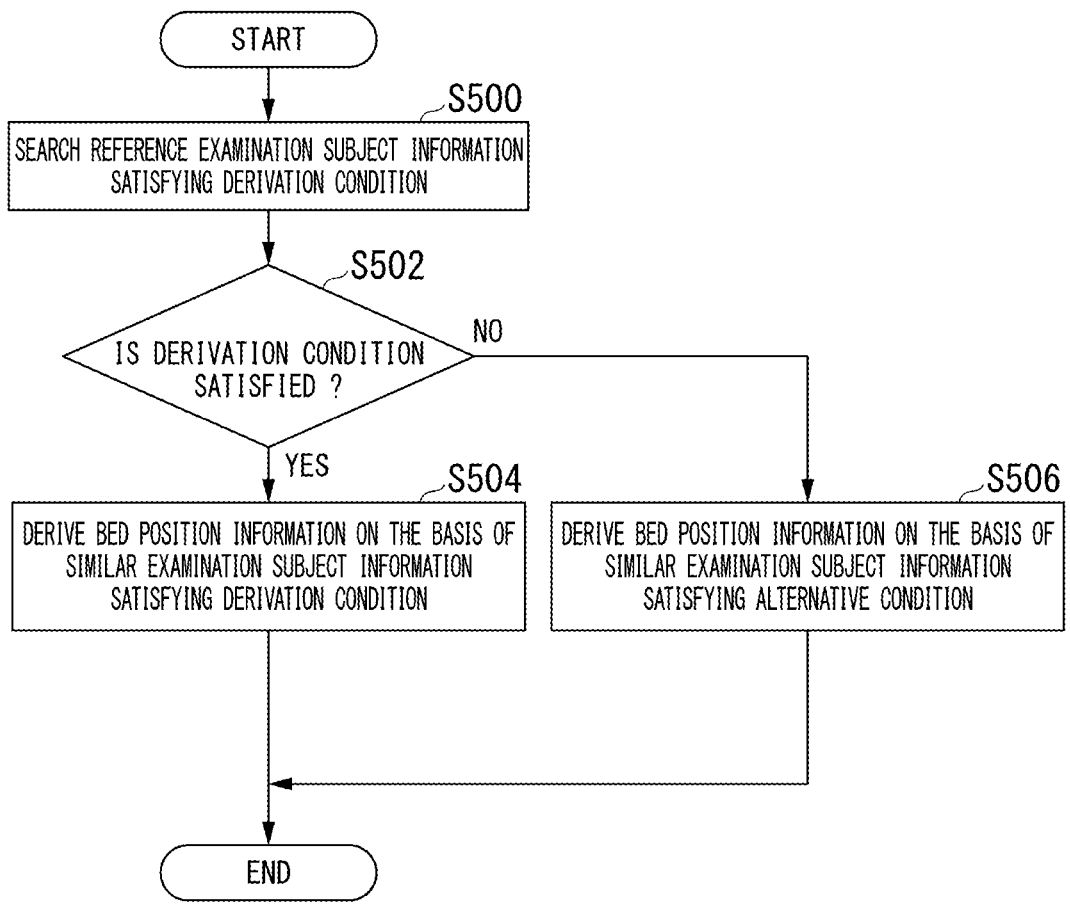
FIG. 24 is a flowchart showing an example of a flow of recommended position derivation processing performed by an automatic alignment function.

FIG. 24 is a flowchart showing an example of a flow of recommended position derivation processing performed by the automatic alignment function 55B-2. The flowchart shown in FIG. 24 corresponds to step S402 of FIG. 23.

The determination function 55B-21 searches reference examination subject information 41-7 which satisfies a derivation condition set in advance (step S500). The derivation condition in step S500 is, for example, a derivation method designated in the input formal F1 of FIG. 21. The determination function 55B-21 determines whether a search result for reference examination subject information 41-7 which satisfies the derivation condition has been acquired (step S502). When it is determined that a search result for reference examination subject information 41-7 which satisfies the derivation condition has been acquired, the processing function 55B-22 derives a recommended position of the top board 33 on the basis of the search result for the reference examination subject information 41-7 which satisfies the derivation condition (step S504). When it is determined that a search result for reference examination subject information 41-7 which satisfies the derivation condition has not been acquired, the processing function 55B-22 derives a recommended position of the top board 33 on the basis of a search result for reference examination subject information 41-7 which satisfies an alternative condition (step S506). The alternative condition in step S506 is, for example, a derivation method designated in the input format F2 of FIG. 21. Hereby, description of processing of this flowchart ends.

Meanwhile, the flowchart shown in FIG. 24 describes a flow of processing when another derivation condition is selected as an alternative condition. When the input format F2-2 is selected as an alternative condition, processing of suspending derivation of a recommended position of the top board 33 is performed in step S506.

According to the X-ray CT apparatus 1B of the above-described third embodiment, it is possible to efficiently perform operations such as alignment of the examination subject P before imaging by including the examination subject information acquisition function 55-1 which acquires examination subject information 41-1 of the examination subject P, the determination function 55B-21 which determines a method for deriving a recommended position information of the top board 33 on the basis of examination subject information 41-1 including physical characteristics data of the examination subject P and information about a imaging target portion, and the processing function 55B-22 which outputs a recommended position of the top board 33 with respect to the examination subject P through the derivation method determined by the determination function 55B-21.

The above-described embodiments can be represented as follows.

A medical image diagnostic apparatus including:
a storage which stores a program; and
a processor,
wherein the processor, by executing the program,
acquires physical characteristics data of an examination subject and information about an imaging target portion, and
outputs bed position information by inputting the physical characteristics data and the information about the imaging target portion to a trained model which is configured to output the bed position information on the basis of the physical characteristics data and the information about the imaging target portion.

According to at least one embodiment described above, it is possible to efficiently perform operations such as alignment of a bed dev ice before imaging by including an acquisition unit (55-1, 55A-1) which is configured to acquire examination subject information (41-1) including physical characteristics data of an examination subject and information about a imaging target portion, and a processing unit (55-2, 55A-2) which is configured to output a recommended position of the bed device (30) by inputting the physical characteristics data of the examination subject and the information about the imaging target portion to a trained model (41-6, 41A-6) which satisfies conditions of the examination subject P.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A medical image diagnostic apparatus, comprising:
a bed device configured to support a top board on which an examination subject is mounted such that the top board can move in a height direction;
processing circuitry configured to:
acquire, from an electronic memory, physical characteristics data of the examination subject and information about an imaging target portion;
control a display to display a plurality of methods for deriving recommended position information of the bed device, the plurality of methods using different reference examination subject information;
determine a method for deriving as selected by an operator among the displayed plurality of methods for deriving;
derive and output bed position information about the examination subject according to the acquired physical characteristics data and the acquired information about the imaging target portion, using the determined method for deriving, the bed position information including a height of the top board with respect to a reference position; and
control the bed device to move the top board to the height included in the output bed position information.

2. The medical image diagnostic apparatus according to claim 1, wherein the determined method for deriving is a derivation method employing other bed position information based on physical characteristics data of another examination subject other than the examination subject, and
wherein the output bed position information of the examination subject includes the other bed position information of the another examination subject having identical imaging conditions as those of the examination subject and a degree of physical characteristics data matching that of the examination subject that is equal to or greater than a predetermined degree.

3. The medical image diagnostic apparatus according to claim 1, wherein the determined method for deriving is a derivation method which derives the bed position information based on physical characteristics data of one or more examination subjects, other than the examination subject, which have identical imaging conditions as those of the examination subject, and wherein the processing circuitry is further configured to derive an average of other bed position information associated with the one or more examination subjects, and uses the average as bed position information of the examination subject.

4. The medical image diagnostic apparatus according to claim 1, wherein the determined method for deriving is a derivation method which selects bed position information based on physical characteristics data of one or more examination subjects other than the examination subject, and wherein the processing circuitry is further configured to output, as the bed position information of the examination subject, other bed position information of another examination subject having an employment condition closest to that of the examination subject from among the one of more examination subjects having identical imaging conditions as those of the examination subject and degrees of physical characteristics data matching that of the examination subject that are equal to or greater than a predetermined degree.

5. The medical image diagnostic apparatus according to claim 4, wherein the employment condition is a condition that an error between the physical characteristics data of the another examination subject and the physical characteristics data of the examination subject is less than a predetermined value.

6. A medical image diagnosis method, using a computer, the method comprising:

acquiring physical characteristics data of an examination subject and information about an imaging target portion;

controlling a display to display a plurality of methods for deriving a recommended position information of a bed device, the plurality of methods using different reference examination subject information;

determining a method for deriving as selected by an operator among the displayed plurality of methods for deriving;

deriving and outputting bed position information about the examination subject according to the acquired physical characteristics data and the acquired information about the imaging target portion, using the determined method for deriving, the bed position information including a height of a top board of the bed device with respect to a reference position, the bed device being configured to support the top board on which the examination subject is mounted such that the top board can move in a height direction; and controlling the bed device to move the top board to the height included in the output bed position information.

7. A non-transitory computer-readable storage medium storing a program causing a computer to:

acquire physical characteristics data of an examination subject and information about an imaging target portion;

control a display to display a plurality of methods for deriving a recommended position information of a bed device, the plurality of methods using different reference examination subject information;

determine a method for deriving as selected by an operator among the displayed plurality of methods for deriving;

derive and output bed position information about the examination subject according to the acquired physical characteristics data and the acquired information about the imaging target portion, using the determined method for deriving, the bed position information including a height of a top board of the bed device with respect to a reference position, the bed device being configured to support the top board on which the examination subject is mounted such that the top board can move in a height direction; and control the bed device to move the top board to the height included in the output bed position information.

8. The medical image diagnostic apparatus according to claim 1, wherein the processing circuitry is further configured to:

determine whether a search result for the reference examination subject information which the determined method for deriving uses has been acquired;

when it is determined that the search result for the reference examination subject information that the determined method for deriving uses has been acquired, derive a recommended position of the bed based on the acquired search result; and when it is determined that the search result for the reference examination subject information that the determined method for deriving uses has not been acquired, derive a recommended position of the bed based on a search result for reference examination subject information which satisfies an alternative condition.

9. The medical image diagnostic apparatus of claim 1, wherein the processing circuitry is further configured to control a medical scanning device to perform a medical scan of the examination subject, which is performed according to the bed position information.

* * * * *